(12) United States Patent
Shibata

(10) Patent No.: US 8,558,012 B2
(45) Date of Patent: Oct. 15, 2013

(54) 2-FLUORO-1,3-BENZODITHIOL 1,1,3,3-TETRAOXIDE DERIVATIVE, PRODUCTION METHOD THEREOF, AND PRODUCTION METHOD OF MONOFLUOROMETHYL GROUP-CONTAINING COMPOUND USING THE SAME

(75) Inventor: Norio Shibata, Aichi (JP)

(73) Assignees: Nagoya Institute of Technology, Aichi (JP); Tosoh F-Tech, Inc., Yamaguchi (JP)

( * ) Notice: Subject to any disclaimer, the term of this patent is extended or adjusted under 35 U.S.C. 154(b) by 169 days.

(21) Appl. No.: 13/254,260

(22) PCT Filed: Feb. 12, 2010

(86) PCT No.: PCT/JP2010/000862
§ 371 (c)(1),
(2), (4) Date: Sep. 1, 2011

(87) PCT Pub. No.: WO2010/100833
PCT Pub. Date: Sep. 10, 2010

(65) Prior Publication Data
US 2011/0319637 A1 Dec. 29, 2011

(30) Foreign Application Priority Data
Mar. 2, 2009 (JP) .................................. 2009-047754

(51) Int. Cl.
*C07D 339/06* (2006.01)
(52) U.S. Cl.
USPC .......................................................... 549/33
(58) Field of Classification Search
USPC .......................................................... 549/33
See application file for complete search history.

(56) References Cited

U.S. PATENT DOCUMENTS 7,638,654 B2 12/2009 Toru et al.
2009/0131723 A1 5/2009 Toru et al.

FOREIGN PATENT DOCUMENTS

| EP | 1 992 612 | 11/2008 |
| JP | 2007-230961 | 9/2007 |
| WO | 2007/100074 | 9/2007 |

OTHER PUBLICATIONS

International Search Report issued Apr. 27, 2010 in International (PCT) Application No. PCT/JP2010/000862, of which the present application is the national stage.
E. P. Kuendig et al., 1,3-Benzodithiole tetraoxide as a $CH_2^{2-}$ synthon, Tetrahedron, vol. 44, No. 22, pp. 6855-6860, 1998.

A. Landa et al., Catalytic Conjugate Additions of Germinal Bis-(sulfone)s: Expanding the Chemistry of Sulfones as Simple Alkyl Anion Equivalents, Chemistry A European Journal, vol. 15, No. 44, pp. 11954-11962, 2009.
Kawazoe et al., Studies of Nucleophilic monofluoromethylation, "Aldehyde ni Taisuru Kyukakuteki Monofluoro Methyl-ka Hanno no Kenkyu", 89th Annual Meeting of Chemical Society of Japan in Spring Koen Yokoshu II, p. 1463, Mar. 13, 2009.
Ogawa et al., Asymmetric Tandem Aldol-cyclization Reaction using trifluoropyruvate, "Kanjo Kozo o Motsu Kyukakuteki Monofluoro Methyl-ka Zai no Sekkei to Gosei", 89th Annual Meeting of Chemical Society of Japan in Spring Koen Yokoshu II, p. 1128, Mar. 13, 2009.
C. Ni et al., Nucleophilic Fluoroalkylation of α,β-Enones, Arynes, and Activated Alkynes with Fluorinated Sulfones: Probing the Hard/Soft Nature of Fluorinated Carbanions, J. Org. Chem., vol. 73, pp. 5699-5713, 2008.
Lucas et al., "The Condensation of Acetaldehyde With Methylmalonic Ester. Methylations with Methyl Bromide", Journal of the American Chemical Society, vol. 51, Aug. 1929, pp. 2535-2538.
Kitamura et al., "A Practical and Convenient Fluorination of 1,3-Dicarbonyl Compounds Using Aqueous HF in the Presence of Iodosylbenzene", Organic Letters, vol. 13, No. 9, 2011, pp. 2392-2394.
International Preliminary Report on Patentability for PCT/JP2010/000862, mailed Sep. 22, 2011.

*Primary Examiner* — Taofiq A Solola
(74) *Attorney, Agent, or Firm* — Wenderoth, Lind & Ponack, L.L.P.

(57) ABSTRACT

A 2-fluoro-1,3-benzodithiol 1,1,3,3-tetraoxide derivative as a monofluoromethyl group introduction agent that is effective as an intermediate in pharmaceutical and agrochemical synthesis, a production method thereof, and a production method of a monofluoromethyl group-containing compound using this 2-fluoro-1,3-benzodithiol 1,1,3,3-tetraoxide derivative are provided. The 2-fluoro-1,3-benzodithiol 1,1,3,3-tetraoxide derivative represented by the following general formula (1) (wherein $R^1$, $R^2$, $R^3$, and $R^4$ each independently represent a hydrogen atom, a straight-chain or branched alkyl group having 1 to 4 carbon atoms, a straight-chain or branched alkyloxy group having 1 to 4 carbon atoms, a halogen atom, a nitro group, or a cyano group), the production method thereof, and various monofluoromethyl group-containing compounds are manufactured using this 2-fluoro-1,3-benzodithiol 1,1,3,3-tetraoxide derivative as a monofluoromethylating agent.

[Formula 1]

(1)

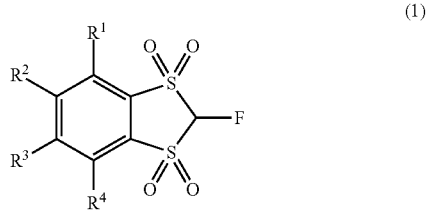

15 Claims, No Drawings

2-FLUORO-1,3-BENZODITHIOL 1,1,3,3-TETRAOXIDE DERIVATIVE, PRODUCTION METHOD THEREOF, AND PRODUCTION METHOD OF MONOFLUOROMETHYL GROUP-CONTAINING COMPOUND USING THE SAME

TECHNICAL FIELD

The present invention relates to a novel 2-fluoro-1,3-benzodithiol 1,1,3,3-tetraoxide derivative, a production method thereof, and a production method of a monofluoromethyl group-containing compound using this 2-fluoro-1,3-benzodithiol 1,1,3,3-tetraoxide derivative. The monofluoromethyl group-containing compound can be effectively used as an intermediate in pharmaceutical and agrochemical synthesis.

BACKGROUND ART

The 2-fluoro-1,3-benzodithiol 1,1,3,3-tetraoxide derivative according to the present invention is not known.

A known example of a conventional technique for introducing a monofluoromethyl group is to use 1-fluoro-1,1-bis(phenylsulfonyl)methane to convert an acetoxy group on a compound having the acetoxy group at an allylic position into a monofluoromethyl group (Patent Literature 1). Other examples include a method in which the same agents are used to convert a silyl group on an aromatic silane compound into a monofluoromethyl group and an addition reaction onto an acetylene compound (Non-Patent Literature 1).

PRIOR ART LITERATURE

Patent Literatures

[Patent Literature 1] Japanese Patent Application Laid-Open No. 2007-230961

Non-Patent Literatures

[Non-Patent Literature 1] Jinbo Hu, et. al., J. Org. Chem., 2008, 73, 5699-5713

SUMMARY OF THE INVENTION

Problems to be Solved by the Invention

The 1-fluoro-1,1-bis(phenylsulfonyl)methane described in the conventional Patent Literature 1 and Non-Patent Literature 1 has a low content of fluoromethylene groups that are converted into a monofluoromethyl group. Further, the applicable reactions are limited to a reaction in which an acetoxy group on a compound having the acetoxy group at an allylic position is converted into a monofluoromethyl group, a method in which a silyl group on an aromatic silane compound is converted into a monofluoromethyl group, and an addition reaction onto an acetylene compound. It was not possible to apply an aldol addition reaction into a carbonyl-containing compound, such as a ketone or an aldehyde, while such an aldol addition reaction is a representative reaction that uses an anion species. Moreover, when deriving the monofluoromethyl group by desulfonating an addition product, depending on the reaction method a large quantity of decomposed matter is generated, so that that there is the problem that the monofluoromethylated product could not be obtained in a high yield.

Means for Solving the Problems

As a result of diligent research concerning methods to resolve the above problems, the present inventors have found a novel 2-fluoro-1,3-benzodithiol 1,1,3,3-tetraoxide derivative having a high content of fluoromethylene groups that are converted into monofluoromethyl groups. Further, the present inventors have also found that this compound could be produced easily in a high yield. In addition, the present inventors have found that the obtained 2-fluoro-1,3-benzodithiol 1,1,3,3-tetraoxide derivative could be utilized to achieve an aldol addition reaction, which is a representative reaction that uses an anion species. Moreover, the present inventors have found that the derivation of the monofluoromethyl groups from the addition product could be carried out in a high yield, without producing byproducts. As a result of these discoveries, the present inventors completed the present invention.

Specifically, the present invention provides the following.

[1] A 2-fluoro-1,3-benzodithiol 1,1,3,3-tetraoxide derivative represented by the following general formula (1),

[Formula 1]

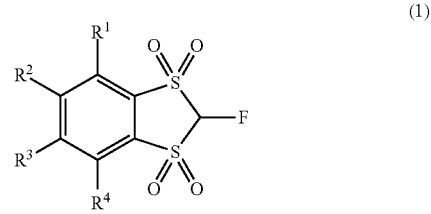

(wherein $R^1$, $R^2$, $R^3$, and $R^4$ each independently represent a hydrogen atom, a straight-chain or branched alkyl group having 1 to 4 carbon atoms, a straight-chain or branched alkyloxy group having 1 to 4 carbon atoms, a halogen atom, a nitro group, or a cyano group).

[2] A 2-fluoro-1,3-benzodithiol 1,1,3,3-tetraoxide, characterized in that in the above-mentioned general formula (1) $R^1$, $R^2$, $R^3$, and $R^4$ are all a hydrogen atom.

[3] A method for producing the 2-fluoro-1,3-benzodithiol 1,1,3,3-tetraoxide derivative according to [1] or [2], characterized by fluorinating a 1,3-benzodithiol 1,1,3,3-tetraoxide derivative represented by the following general formula (2),

[Formula 2]

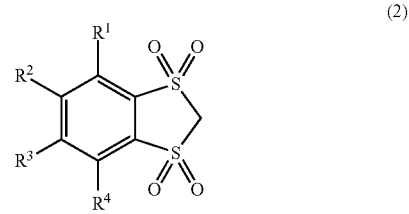

(wherein $R^1$, $R^2$, $R^3$, and $R^4$ are as described above)
with an electrophilic fluorinating agent.

[4] A monofluoromethyl group introduction agent comprising the 2-fluoro-1,3-benzodithiol 1,1,3,3-tetraoxide derivative according to [1] or [2].

[5] A method for producing a 2-substituted-2-fluoro-1,3-benzodithiol 1,1,3,3-tetraoxide derivative represented by the following general formula (4),

[Formula 4]

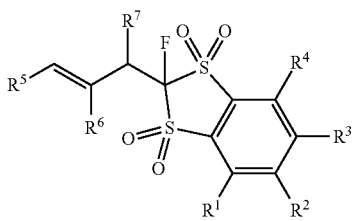

(4)

(wherein $R^1$, $R^2$, $R^3$, and $R^4$ are as described above; $R^5$ represents a hydrogen atom, a methyl group, an ethyl group, a straight-chain, branched, or cyclic alkyl group having 3 to 10 carbon atoms, an optionally-substituted phenyl group, a 1-naphthyl group, or a 2-naphthyl group; $R^6$ represents a hydrogen atom, a methyl group, an ethyl group, an n-propyl group, an isopropyl group, or a benzyl group; $R^7$ represents a hydrogen atom, a methyl group, an ethyl group, a straight-chain, branched, or cyclic alkyl group having 3 to 10 carbon atoms, a phenyl group, an acetoxy group, a methoxy group, an ethoxy group, or a straight-chain, branched, or cyclic alkyloxy group having 3 to 10 carbon atoms), characterized by reacting, in the presence of a metal catalyst, an acetate represented by the following general formula (3),

[Formula 3]

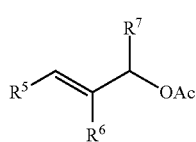

(3)

(wherein $R^5$, $R^6$, and $R^7$ are as described above)
and the 2-fluoro-1,3-benzodithiol 1,1,3,3-tetraoxide derivative according to [1], [2], or [4].

[6] The method for producing a 2-substituted-2-fluoro-1,3-benzodithiol 1,1,3,3-tetraoxide derivative according to [5], characterized in that $R^1$, $R^2$, $R^3$, and $R^4$ are a hydrogen atom and $R^7$ is an acetoxy group.

[7] A method for producing a monofluoromethyl group-containing compound represented by the following general formula (5),

[Formula 5]

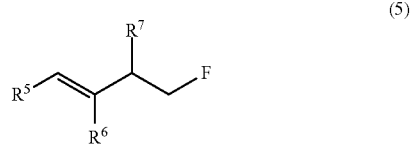

(5)

(wherein $R^5$, $R^6$, and $R^7$ are as described above)
characterized by reacting, in the presence of a metal catalyst, the acetate represented by the general formula (3) according to [6] and the 2-fluoro-1,3-benzpdithiol 1,1,3,3-tetraoxide derivative according to [1], [2], or [4] to obtain the 2-substituted-2-fluoro-1,3-benzodithiol 1,1,3,3-tetraoxide derivative represented by the above-mentioned general formula (4), and then reducing the resultant product.

[8] A method for producing a monofluoromethyl group-containing compound represented by the following general formula (6),

[Formula 6]

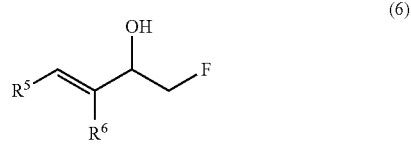

(6)

(wherein $R^5$ and $R^6$ are as described above)
characterized by producing the 2-substituted-2-fluoro-1,3-benzodithiol 1,1,3,3-tetraoxide derivative according to [6] in which $R^2$, $R^3$, and $R^4$ are a hydrogen atom and $R^7$ is an acetoxy group, then hydrolyzing and subsequently reducing the resultant product.

[9] A method for producing an optically-active 2-substituted-2-fluoro-1,3-benzodithiol 1,1,3,3-tetraoxide derivative represented by the following general formula (7),

[Formula 7]

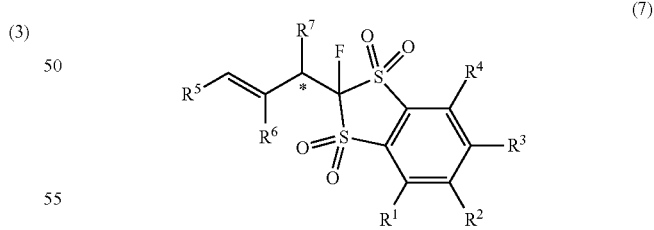

(7)

(wherein * represents an asymmetric carbon $R^1$, $R^2$, $R^3$, $R^4$, $R^5$, $R^6$, and $R^7$ are as described above)
characterized by reacting, in the presence of an optically active ligand and a metal catalyst, an acetate represented by the above-mentioned general formula (3) and the 2-fluoro-1,3-benzodithiol 1,1,3,3-tetraoxide derivative according to [1], [2], or [4].

[10] The method for producing an optically-active 2-substituted-2-fluoro-1,3-benzodithiol 1,1,3,3-tetraoxide derivative according to [9], characterized in that $R^1$, $R^2$, $R^3$, and $R^4$ are a hydrogen atom and $R^7$ is an acetoxy group.

[11] A method for producing an optically-active monofluoromethyl group-containing compound represented by the following general formula (8),

[Formula 8]

(8)

$R^5$, $R^6$, $R^7$, F (structure with * chiral center)

(wherein $R^5$, $R^6$, and $R^7$ are as described above)
characterized by producing the optically-active 2-substituted-2-fluoro-1,3-benzodithiol 1,1,3,3-tetraoxide derivative according to [9], then hydrolyzing and subsequently reducing the resultant product.

[12] A method for producing an optically-active monofluoromethyl group-containing compound represented by the following general formula (9),

[Formula 9]

(9)

$R^5$, $R^6$, OH, F (structure with * chiral center)

(wherein *, $R^5$ and $R^6$ are as described above)
characterized by producing the optically-active 2-substituted-2-fluoro-1,3-benzodithiol 1,1,3,3-tetraoxide derivative according to [10] in which $R^1$, $R^2$, $R^3$, and $R^4$ are a hydrogen atom and $R^7$ is an acetoxy group, then hydrolyzing and subsequently reducing the resultant product.

[13] A method for producing a 2-substituted-2-fluoro-1,3-benzodithiol 1,1,3,3-tetraoxide derivative represented by the following general formula (11),

[Formula 11]

(11)

(structure showing $R^9$, $R^8$, OH, F, S(=O)$_2$ groups, and $R^1$, $R^2$, $R^3$, $R^4$ on benzene ring)

(wherein $R^1$, $R^2$, $R^3$, and $R^4$ are as described above; $R^8$ and $R^9$ each independently represents a hydrogen atom, a methyl group, an ethyl group, a straight-chain, branched, or cyclic alkyl group having 3 to 10 carbon atoms, an optionally-substituted phenyl group, a 1-naphthyl group, a 2-naphthyl group, or a phenylethylene group; and $R^8$ and $R^9$ are not simultaneously a hydrogen atom)
characterized by reacting, in the presence of a base, a carbonyl-containing compound represented by the following general formula (10),

[Formula 10]

(10)

$R^8$—C(=O)—$R^9$ (wherein $R^8$ and $R^9$ are as described above) and the 2-fluoro-1,3-benzodithiol 1,1,3,3-tetraoxide derivative according to [1], [2], or [4].

[14] A method for producing the 2-substituted-2-fluoro-1,3-benzodithiol 1,1,3,3-tetraoxide derivative according to [12], characterized in that $R^1$, $R^2$, $R^3$, $R^4$, and $R^9$ are a hydrogen atom.

[15] A method for producing a monofluoromethyl group-containing compound represented by the following general formula (11),

[Formula 12]

(12)

$R^9$, $R^8$, OH, F (wherein $R^8$ and $R^9$ are as described above)
characterized by producing the 2-substituted-2-fluoro-1,3-benzodithiol 1,1,3,3-tetraoxide derivative according to [12], and then reducing the resultant product.

[16] A method for producing a monofluoromethyl group-containing compound represented by the following general formula (12),

[Formula 13]

(13)

$R^8$, OH, F (wherein $R^8$ is as described above)
characterized by producing the 2-substituted-2-fluoro-1,3-benzodithiol 1,1,3,3-tetraoxide derivative according to [13] in which $R^1$, $R^2$, $R^3$, $R^4$, and $R^9$ are a hydrogen atom, then reducing the resultant product.

Advantages of the Invention

According to the present invention, a wider range of reactions can be applied than conventionally-known monofluoromethylating agents, and the content of fluoromethylene groups to be converted into monofluoromethyl groups is high. In addition, the present invention can also be applied to an asymmetric reaction. Consequently, the present invention can provide a more industrial monofluoromethylating agent.

BEST MODE FOR CARRYING OUT THE INVENTION

The present invention will now be described in more detail.
Examples of the straight-chain or branched alkyl group having 1 to 4 carbon atoms include a methyl group, an ethyl group, an n-propyl group, an iso-propyl group, an n-butyl group, and a tert-butyl group.

Examples of the straight-chain or branched alkyloxy group having 1 to 4 carbon atoms include a methoxy group, an ethoxy group, an n-propoxy group, an iso-propoxy group, an n-butoxy group, and a tert-butoxy group.

The optionally-substituted phenyl group is an unsubstituted phenyl group or a substituted phenyl group in which 1 to 5 hydrogens on the arbitrary positions of a benzene ring are substituted. Examples of the substituents include a fluorine atom, a chlorine atom, a bromine atom, a methyl group, an ethyl group, a straight-chain, branched, or cyclic alkyl group having 3 to 10 carbon atoms, a methoxy group, an ethoxy group, and a straight-chain, branched, or cyclic alkyloxy group having 3 to 10 carbon atoms.

Examples of the halogen atom include a fluorine atom, a chlorine atom, and a bromine atom.

Examples of the straight-chain, branched, or cyclic alkyl group having 3 to 10 carbon atoms include an n-propyl group, an iso-propyl group, an n-butyl group, a tert-butyl group, an n-pentyl group, an n-hexyl group, an n-heptyl group, an n-octyl group, an n-nonyl group, an n-decyl group, a 3-methylbutyl group, a 4-methylpentyl group, a 5-methylhexyl group, a 6-methylheptyl group, a 7-methyloctyl group, an 8-methylnonyl group, a cyclohexyl group, and a cyclohexylmethyl group.

Examples of the straight-chain, branched, or cyclic alkyloxy group having 3 to 10 carbon atoms include an n-propoxy group, an iso-pro propoxy group, an n-butoxy group, a tert-butoxy group, an n-pentyloxy group, an n-hexyloxy group, an n-heptyloxy group, an n-octyloxy group, an n-nonyloxy group, an n-decyloxy group, a 3-methylbutoxy group, a 4-methylpentyloxy group, a 5-methylhexyloxy group, a 6-methylheptyloxy group, a 7-methyloctyloxy group, an 8-methylnonyloxy group, a cyclohexyloxy group, and a cyclohexylmethoxy group.

Specific examples of the 2-fluoro-1,3-benzodithiol 1,1,3,3-tetraoxide derivative represented by the above general formula (1) according to the present invention include 2-fluoro-1,3-benzodithiol 1,1,3,3-tetraoxide, 2-fluoro-1,3-(1-methylbenzo)dithiol 1,1,3,3-tetraoxide, 2-fluoro-1,3-(2-methylbenzo)dithiol 1,1,3,3-tetraoxide, 2-fluoro-1,3-(1-ethylbenzo)dithiol 1,1,3,3-tetraoxide, 2-fluoro-1,3-(2-ethylbenzo)dithiol 1,1,3,3-tetraoxide, 2-fluoro-1,3-(1-n-propylbenzo)dithiol 1,1,3,3-tetraoxide, 2-fluoro-1,3-(2-n-propylbenzo)dithiol 1,1,3,3-tetraoxide, 2-fluoro-1,3-(1-iso-propylbenzo)dithiol 1,1,3,3-tetraoxide, 2-fluoro-1,3-(2-iso-propylbenzo)dithiol 1,1,3,3-tetraoxide, 2-fluoro-1,3-(1-n-butylbenzo)dithiol 1,1,3,3-tetraoxide, 2-fluoro-1,3-(2-n-butylbenzo)dithiol 1,1,3,3-tetraoxide, 2-fluoro-1,3-(1-tert-butylbenzo)dithiol 1,1,3,3-tetraoxide, 2-fluoro-1,3-(2-tert-butylbenzo)dithiol 1,1,3,3-tetraoxide, 2-fluoro-1,3-(1-methoxybenzo)dithiol 1,1,3,3-tetraoxide, 2-fluoro-1,3-(2-methoxybenzo)dithiol 1,1,3,3-tetraoxide, 2-fluoro-1,3-(1-ethoxybenzo)dithiol 1,1,3,3-tetraoxide, 2-fluoro-1,3-(2-ethoxybenzo)dithiol 1,1,3,3-tetraoxide, 2-fluoro-1,3-(1-n-propoxybenzo)dithiol 1,1,3,3-tetraoxide, 2-fluoro-1,3-(2-n-propoxybenzo)dithiol 1,1,3,3-tetraoxide, 2-fluoro-1,3-(1-iso-propoxybenzo)dithiol 1,1,3,3-tetraoxide, 2-fluoro-1,3-(2-iso-propoxybenzo)dithiol 1,1,3,3-tetraoxide, 2-fluoro-1,3-(1-n-butoxybenzo)dithiol 1,1,3,3-tetraoxide, 2-fluoro-1,3-(2-n-butoxybenzo)dithiol 1,1,3,3-tetraoxide, 2-fluoro-1,3-(1-tert-butoxybenzo)dithiol 1,1,3,3-tetraoxide, 2-fluoro-1,3-(2-tert-butoxybenzo)dithiol 1,1,3,3-tetraoxide, 2-fluoro-1,3-(1-fluorobenzo)dithiol 1,1,3,3-tetraoxide, 2-fluoro-1,3-(2-fluorobenzo)dithiol 1,1,3,3-tetraoxide, 2-fluoro-1,3-(1-chlorobenzo)dithiol 1,1,3,3-tetraoxide, 2-fluoro-1,3-(2-chlorobenzo)dithiol 1,1,3,3-tetraoxide, 2-fluoro-1,3-(1-bromobenzo)dithiol 1,1,3,3-tetraoxide, 2-fluoro-1,3-(2-bromobenzo)dithiol 1,1,3,3-tetraoxide, 2-fluoro-1,3-(1-nitrobenzo)dithiol 1,1,3,3-tetraoxide, 2-fluoro-1,3-(2-nitrobenzo)dithiol 1,1,3,3-tetraoxide, 2-fluoro-1,3-(1-cyanobenzo)dithiol 1,1,3,3-tetraoxide, and 2-fluoro-1,3-(2-cyanobenzo)dithiol 1,1,3,3-tetraoxide.

The 2-fluoro-1,3-benzodithiol 1,1,3,3-tetraoxide derivative represented by the general formula (1) according to the present invention can be produced by fluorinating an applicable 1,3-(4-cyanobenzo)dithiol 1,1,3,3-tetraoxide derivative with an electrophilic fluorinating agent in an organic solvent, for example.

Specific examples of electrophilic fluorinating agents that can be used to produce the 2-fluoro-1,3-benzodithiol 1,1,3,3-tetraoxide derivative represented by the general formula (1) according to the present invention include 1-chloromethyl-4-fluoro-1,4-diazabicyclo[2.2.2]octane bis(tetrafluoroborate), N-fluoro-2,4,6-trimethylpyridinium tetrafluoroborate, N-fluoropyridinium tetrafluoroborate, N-fluoro-2,6-dichloropyridinium tetrafluoroborate, N-fluoro-2,4,6-trimethylpyridinium trifluoromethanesulfonate, N-fluoropyridinium trifluoromethanesulfonate, N-fluoro-2,6-dichloropyridinium trifluoromethanesulfonate, 1,1'-difluoro-2,2'-bipyridinium bis(tetrafluoroborate), N-fluoro-4,6-dimethylpyridinium-2-sulfonate, N-fluoro-4-methylpyridinium-2-sulfonate, N-fluoro-5-(trifluoromethyl)pyridinium-2-sulfonate, N-fluoro-3-chloro-5-(trifluoromethyl)pyridinium-2-sulfonate, and N-fluoro-4,6-bis(trifluoromethyl)pyridinium-2-sulfonate. The used amount of the electrophilic fluorinating agent may be 0.6 to 2.0 moles with respect to the 1,3-benzodithiol 1,1,3,3-tetraoxide derivative used in the reaction.

As the solvent used in the production of the 2-fluoro-1,3-benzodithiol 1,1,3,3-tetraoxide derivative represented by the general formula (1) according to the present invention, any solvent may be used as long as it is inert in the reaction. Specific examples thereof include halogenated hydrocarbons such as dichloromethane and chloroform, alcohols such as methanol, ethanol, iso-propanol, and tert-butanol, nitriles such as acetonitrile and propionitrile, and aromatic hydrocarbons such as toluene, xylene, and ethylbenzene. The solvent may be used alone or as a mixture. The solvent may be used in an amount that is 10 to 1,000 times by weight the 1,3-benzodithiol 1,1,3,3-tetraoxide derivative used in the reaction.

During the production of the 2-fluoro-1,3-benzodithiol 1,1,3,3-tetraoxide derivative represented by the general formula (1) according to the present invention, after preparing a salt of the 2-fluoro-1,3-benzodithiol 1,1,3,3-tetraoxide derivative using a base, this salt may be reacted with the above electrophilic fluorinating agent. Specific examples of bases that can be used include lithium hydride, sodium hydride, potassium hydride, sodium methoxide, potassium methoxide, sodium ethoxide, potassium ethoxide, sodium tert-butoxide, and potassium tert-butoxide. The used amount of the base is 0.8 to 2 moles with respect to the 1,3-benzodithiol 1,1,3,3-tetraoxide derivative used in the reaction. The reaction is completed at a reaction temperature when preparing the salt using the base in a temperature range of −20 to 50° C., and with a reaction time of 0.5 to 8 hours.

Although the reaction temperature and time when producing the 2-fluoro-1,3-benzodithiol 1,1,3,3-tetraoxide derivative represented by the general formula (1) according to the present invention depend on the substrate used in the reaction, the type of used electrophilic fluorinating agent, whether a base is used, and the type of used solvent, generally, the target 2-fluoro-1,3-benzodithiol 1,1,3,3-tetraoxide derivative can be obtained by reacting for 1 to 24 hours and at a temperature that is at or lower than the boiling point of the used solvent and in a temperature range of −20 to 80° C.

The 2-fluoro-1,3-benzodithiol 1,1,3,3-tetraoxide derivative represented by the general formula (1) according to the present invention is used as an introduction agent for a monofluoromethyl group precursor in a nucleophilic reaction. Examples of reactions that can be employed include an addition reaction into a π-allyl complex derived from allyl acetate, which is possible with a conventional agent, and an aldol addition reaction into a carbonyl-containing compound, which was impossible with a conventional agent.

The reaction of the 2-fluoro-1,3-benzodithiol 1,1,3,3-tetraoxide derivative represented by the general formula (1) according to the present invention and allyl acetate can be carried out in a reaction-inert solvent in the presence of a metal catalyst.

Specific examples of allyl acetates that can use the 2-fluoro-1,3-benzodithiol 1,1,3,3-tetraoxide derivative represented by the general formula (1) according to the present invention as an introduction agent for a monofluoromethyl group precursor include, but are not limited to, 1-acetoxy-2-propene, 1-acetoxy-2-butene, 1-acetoxy-2-pentene, 1-acetoxy-2-hexene, 1-acetoxy-2-heptene, 1-acetoxy-2-octene, 1-acetoxy-2-nonene, 1-acetoxy-2-decene, 1-acetoxy-3-cyclohexyl-2-propene, 1-acetoxy-2-methyl-2-propene, 1-acetoxy-2-methyl-2-butene, 1-acetoxy-2-methyl-2-pentene, 1-acetoxy-2-methyl-2-hexene, 1-acetoxy-2-methyl-2-heptene, 1-acetoxy-2-methyl-2-octene, 1-acetoxy-2-methyl-2-nonene, 1-acetoxy-2-methyl-2-decene, 1-acetoxy-2-ethyl-2-propene, 1-acetoxy-2-ethyl-2-butene, 1-acetoxy-2-ethyl-2-pentene, 1-acetoxy-2-ethyl-2-hexene, 1-acetoxy-2-ethyl-2-heptene, 1-acetoxy-2-ethyl-2-octene, 1-acetoxy-2-ethyl-2-nonene, 1-acetoxy-2-ethyl-2-decene, 1-acetoxy-3-cyclohexyl-2-ethyl-2-propene, 1-acetoxy-2-n-propyl-2-propene, 1-acetoxy-2-n-propyl-2-butene, 1-acetoxy-2-n-propyl-2-pentene, 1-acetoxy-2-n-propyl-2-hexene, 1-acetoxy-2-n-propyl-2-heptene, 1-acetoxy-2-n-propyl-2-octene, 1-acetoxy-2-n-propyl-2-nonene, 1-acetoxy-2-n-propyl-2-decene, 1-acetoxy-3-cyclohexyl-2-n-propyl-2-propene, 1-acetoxy-2-iso-propyl-2-propene, 1-acetoxy-2-iso-propyl-2-butene, 1-acetoxy-2-iso-propyl-2-pentene, 1-acetoxy-2-iso-propyl-2-hexene, 1-acetoxy-2-iso-propyl-2-heptene, 1-acetoxy-2-iso-propyl-2-octene, 1-acetoxy-2-iso-propyl-2-nonene, 1-acetoxy-2-iso-propyl-2-decene, 1-acetoxy-3-cyclohexyl-2-iso-propyl-2-propene, 1-acetoxy-2-phenylmethyl-2-propene, 1-acetoxy-2-phenylmethyl-2-butene, 1-acetoxy-2-phenylmethyl-2-pentene, 1-acetoxy-2-phenylmethyl-2-hexene, 1-acetoxy-2-phenylmethyl-2-heptene, 1-acetoxy-2-phenylmethyl-2-octene, 1-acetoxy-2-phenylmethyl-2-nonene, 1-acetoxy-2-phenylmethyl-2-decene, 1-acetoxy-3-cyclohexyl-2-phenylmethyl-2-propene, 1-acetoxy-3-phenyl-2-propene, 1-acetoxy-3-(2-fluorophenyl)-2-propene, 1-acetoxy-3-(3-fluorophenyl)-2-propene, 1-acetoxy-3-(4-fluorophenyl)-2-propene, 1-acetoxy-3-(2-chlorophenyl)-2-propene, 1-acetoxy-3-(3-chlorophenyl)-2-propene, 1-acetoxy-3-(4-chlorophenyl)-2-propene, 1-acetoxy-3-(2-bromophenyl)-2-propene, 1-acetoxy-3-(3-bromophenyl)-2-propene, 1-acetoxy-3-(4-bromophenyl)-2-propene, 1-acetoxy-3-(2-methylphenyl)-2-propene, 1-acetoxy-3-(3-methylphenyl)-2-propene, 1-acetoxy-3-(4-methylphenyl)-2-propene, 1-acetoxy-3-(2-ethylphenyl)-2-propene, 1-acetoxy-3-(3-ethylphenyl)-2-propene, 1-acetoxy-3-(4-ethylphenyl)-2-propene, 1-acetoxy-3-(2-n-propylphenyl)-2-propene, 1-acetoxy-3-(3-n-propylphenyl)-2-propene, 1-acetoxy-3-(4-n-propylphenyl)-2-propene, 1-acetoxy-3-(2-iso-propylphenyl)-2-propene, 1-acetoxy-3-(3-iso-propylphenyl)-2-propene, 1-acetoxy-3-(4-iso-propylphenyl)-2-propene, 1-acetoxy-3-(2-n-butylphenyl)-2-propene, 1-acetoxy-3-(3-n-butylphenyl)-2-propene, 1-acetoxy-3-(4-n-butylphenyl)-2-propene, 1-acetoxy-3-(2-tert-butylphenyl)-2-propene, 1-acetoxy-3-(3-tert-butylphenyl)-2-propene, 1-acetoxy-3-(4-tert-butylphenyl)-2-propene, 1-acetoxy-3-(4-n-pentylphenyl)-2-propene, 1-acetoxy-(4-n-hexylphenyl)-2-propene, 1-acetoxy-3-(4-n-heptylphenyl)-2-propene, 1-acetoxy-3-(4-n-octylphenyl)-2-propene, 1-acetoxy-3-(4-n-nonylphenyl)-2-propene, 1-acetoxy-3-(4-n-decylphenyl)-2-propene, 1-acetoxy-2-methyl-3-phenyl-2-propene, 1-acetoxy-2-methyl-3-(2-fluorophenyl)-2-propene, 1-acetoxy-2-methyl-3-(3-fluorophenyl)-2-propene, 1-acetoxy-2-methyl-3-(4-fluorophenyl)-2-propene, 1-acetoxy-2-methyl-3-(2-chlorophenyl)-2-propene, 1-acetoxy-2-methyl-3-(3-chlorophenyl)-2-propene, 1-acetoxy-2-methyl-3-(4-chlorophenyl)-2-propene, 1-acetoxy-2-methyl-3-(2-bromophenyl)-2-propene, 1-acetoxy-2-methyl-3-(3-bromophenyl)-2-propene, 1-acetoxy-2-methyl-3-(4-bromophenyl)-2-propene, 1-acetoxy-2-methyl-3-(2-methylphenyl)-2-propene, 1-acetoxy-2-methyl-3-(3-methylphenyl)-2-propene, 1-acetoxy-2-methyl-3-(4-methylphenyl)-2-propene, 1-acetoxy-2-methyl-3-(2-ethylphenyl)-2-propene, 1-acetoxy-2-methyl-3-(3-ethylphenyl)-2-propene, 1-acetoxy-2-methyl-3-(4-ethylphenyl)-2-propene, 1-acetoxy-2-methyl-3-(2-n-propylphenyl)-2-propene, 1-acetoxy-2-methyl-3-(3-n-propylphenyl)-2-propene, 1-acetoxy-2-methyl-3-(4-n-propylphenyl)-2-propene, 1-acetoxy-2-methyl-3-(2-iso-propylphenyl)-2-propene, 1-acetoxy-2-methyl-3-(3-iso-propylphenyl)-2-propene, 1-acetoxy-2-methyl-3-(4-iso-propylphenyl)-2-propene, 1-acetoxy-2-methyl-3-(2-n-butylphenyl)-2-propene, 1-acetoxy-2-methyl-3-(3-n-butylphenyl)-2-propene, 1-acetoxy-2-methyl-3-(4-n-butylphenyl)-2-propene, 1-acetoxy-2-methyl-3-(2-tert-butylphenyl)-2-propene, 1-acetoxy-2-methyl-3-(3-tert-butylphenyl)-2-propene, 1-acetoxy-2-methyl-3-(4-tert-butylphenyl)-2-propene, 1-acetoxy-2-methyl-3-(4-n-pentylphenyl)-2-propene, 1-acetoxy-2-methyl-3-(4-n-hexylphenyl)-2-propene, 1-acetoxy-2-methyl-3-(4-n-heptylphenyl)-2-propene, 1-acetoxy-2-methyl-3-(4-n-octylphenyl)-2-propene, 1-acetoxy-2-methyl-3-(4-n-nonylphenyl)-2-propene, 1-acetoxy-2-methyl-3-(4-n-decylphenyl)-2-propene, 1-acetoxy-2-ethyl-3-phenyl-2-propene, 1-acetoxy-2-ethyl-3-(2-fluorophenyl)-2-propene, 1-acetoxy-2-ethyl-3-(3-fluorophenyl)-2-propene, 1-acetoxy-2-ethyl-3-(4-fluorophenyl)-2-propene, 1-acetoxy-2-ethyl-3-(2-chlorophenyl)-2-propene, 1-acetoxy-2-ethyl-3-(3-chlorophenyl)-2-propene, 1-acetoxy-2-ethyl-3-(4-chlorophenyl)-2-propene, 1-acetoxy-2-ethyl-3-(2-bromophenyl)-2-propene, 1-acetoxy-2-ethyl-3-(3-bromophenyl)-2-propene, 1-acetoxy-2-ethyl-3-(4-bromophenyl)-2-propene, 1-acetoxy-2-ethyl-3-(2-methylphenyl)-2-propene, 1-acetoxy-2-ethyl-3-(3-methylphenyl)-2-propene, 1-acetoxy-2-ethyl-3-(4-methylphenyl)-2-propene, 1-acetoxy-2-ethyl-3-(2-ethylphenyl)-2-propene, 1-acetoxy-2-ethyl-3-(3-ethylphenyl)-2-propene, 1-acetoxy-2-ethyl-3-(4-ethylphenyl)-2-propene, 1-acetoxy-2-ethyl-3-(2-n-propylphenyl)-2-propene, 1-acetoxy-2-ethyl-3-(3-n-propylphenyl)-2-propene, 1-acetoxy-2-ethyl-3-(4-n-propylphenyl)-2-propene, 1-acetoxy-2-ethyl-3-(2-iso-propylphenyl)-2-propene, 1-acetoxy-2-ethyl-3-(3-iso-propylphenyl)-2-propene, 1-acetoxy-1-ethyl-3-(4-iso-propylphenyl)-2-propene, 1-acetoxy-2-ethyl-3-(2-n-butylphenyl)-2-propene, 1-acetoxy-2-ethyl-3-(3-n-butylphenyl)-2-propene, 1-acetoxy-2-ethyl-3-(4-n-butylphenyl)-2-propene, 1-acetoxy-2-ethyl-3-(2-tertbutylphenyl)-2-propene, 1-acetoxy-2-ethyl-3-(3-tert-butylphenyl)-2-propene, 1-acetoxy-2-ethyl-3-(4-tert-butylphenyl)-2-propene, 1-acetoxy-2-ethyl-3-(4-n-pentylphenyl)-2-propene, 1-acetoxy-2-ethyl-3-(4-n-hexylphenyl)-2-propene, 1-acetoxy-2-ethyl-3-(4-n-heptylphenyl)-2-propene, 1-acetoxy-2-ethyl-3-(4-n-octylphenyl)-2-propene, 1-acetoxy-2-ethyl-3-(4-n-nonylphenyl)-2-propene. 1-acetoxy-2-ethyl-3-(4-n-decylphenyl)-2-propene, 1-acetoxy-2-n-propyl-3-phenyl-2-propene, 1-acetoxy-2-n-propyl-3-(2-fluorophenyl)-2-propene, 1-acetoxy-2-n-propyl-3-(3-fluorophenyl)-2-propene, 1-acetoxy-2-n-propyl-3-(4-fluorophenyl)-2-propene, 1-acetoxy-2-n-propyl-3-(2-chlorophenyl)-2-propene, 1-acetoxy-2-n-propyl-3-(3-chlorophenyl)-2-propene, 1-acetoxy-2-n-propyl-3-(4-chlorophenyl)-2-propene, 1-acetoxy-2-n-propyl-3-(2-bromophenyl)-2-propene, 1-acetoxy-2-n-propyl-3-(3-bromophenyl)-2-propene, 1-acetoxy-2-n-propyl-3-(4-bromophenyl)-2-propene, 1-acetoxy-2-n-propyl-3-(2-methylphenyl)-2-propene, 1-acetoxy-2-n-propyl-3-(3-methylphenyl)-2-propene, 1-acetoxy-2-n-propyl-3-(4-methylphenyl)-2-propene, 1-acetoxy-2-n-propyl-3-(2-ethylphenyl)-2-propene, 1-acetoxy-2-n-propyl-3-(3-ethylphenyl)-2-propene, 1-acetoxy-2-n-propyl-3-(4-ethylphenyl)-2-propene, 1-acetoxy-2-n-propyl-3-(2-n-propylphenyl)-2-propene, 1-acetoxy-2-n-propyl-3-(3-n-propylphenyl)-2-propene, 1-acetoxy-2-n-propyl-3-(4-n-propylphenyl)-2-propene, 1-acetoxy-2-n-propyl-3-(2-iso-propylphenyl)-2-propene. 1-acetoxy-2-n-propyl-3-(3-iso-propylphenyl)-2-propene, 1-acetoxy-2-n-propyl-3-(4-iso-propylphenyl)-2-propene, 1-acetoxy-2-n-propyl-3-(2-n-butylphenyl)-2-propene, 1-acetoxy-2-n-propyl-3-(3-n-butylphenyl)-2-propene, 1-acetoxy-2-n-propyl-3-(4-n-butylphenyl)-2-propene, 1-acetoxy-2-n-propyl-3-(2-tert-butylphenyl)-2-propene, 1-acetoxy-2-n-propyl-3-(3-tert-butylphenyl)-2-propene, 1-acetoxy-2-n-propyl-3-(4-tert-butylphenyl)-2-propene, 1-acetoxy-2-n-propyl-3-(4-n-pentylphenyl)-2-propene, 1-acetoxy-2-n-propyl-3-(4-n-hexylphenyl)-2-propene, 1-acetoxy-2-n-propyl-3-(4-n-heptylphenyl)-2-propene, 1-acetoxy-2-n-propyl-3-(4-n-octylphenyl)-2-propene. 1-acetoxy-2-n-propyl-3-(4-n-nonylphenyl)-2-propene, 1-acetoxy-2-n-propyl-3-(4-n-decylphenyl)-2-propene, 1-acetoxy-2-iso-propyl-3-phenyl-2-propene, 1-acetoxy-2-iso-propyl-3-(2-fluorophenyl)-2-propene, 1-acetoxy-2-iso-propyl-3-(3-fluorophenyl)-2-propene, 1-acetoxy-2-iso-propyl-3-(4-fluorophenyl)-2-propene, 1-acetoxy-2-iso-propyl-3-(2-chlorophenyl)-2-propene, 1-acetoxy-2-iso-propyl-3-(3-chlorophenyl)-2-propene, 1-acetoxy-2-iso-propyl-3-(4-chlorophenyl)-2-propene, 1-acetoxy-2-iso-propyl-3-(2-bromophenyl)-2-propene, 1-acetoxy-2-iso-propyl-3-(3-bromophenyl)-2-propene, 1-acetoxy-2-iso-propyl-3-(4-bromophenyl)-2-propene, 1-acetoxy-2-iso-propyl-3-(2-methylphenyl)-2-propene, 1-acetoxy-2-iso-propyl-3-(3-methylphenyl)-2-propene, 1-acetoxy-2-iso-propyl-3-(4-methylphenyl)-2-propene, 1-acetoxy-2-iso-propyl-3-(2-ethylphenyl)-2-propene, 1-acetoxy-2-iso-propyl-3-(3-ethylphenyl)-2-propene, 1-acetoxy-2-iso-propyl-3-(4-ethylphenyl)-2-propene, 1-acetoxy-2-iso-propyl-3-(2-n-propylphenyl)-2-propene, 1-acetoxy-2-iso-propyl-3-(3-n-propylphenyl)-2-propene, 1-acetoxy-2-iso-propyl-3-(4-n-propylphenyl)-2-propene, 1-acetoxy-2-iso-propyl-3-(2-iso-propylphenyl)-2-propene, 1-acetoxy-2-iso-propyl-3-(3-iso-propylphenyl)-2-propene, 1-acetoxy-2-iso-propyl-3-(4-iso-propylphenyl)-2-propene, 1-acetoxy-2-iso-propyl-3-(2-n-butylphenyl)-2-propene, 1-acetoxy-2-iso-propyl-3-(3-n-butylphenyl)-2-propene, 1-acetoxy-2-iso-propyl-3-(4-n-butylphenyl)-2-propene, 1-acetoxy-2-iso-propyl-3-(2-tert-butylphenyl)-2-propene, 1-acetoxy-2-iso-propyl-3-(3-tert-butylphenyl)-2-propene, 1-acetoxy-2-iso-propyl-3-(4-tert-butylphenyl)-2-propene, 1-acetoxy-2-iso-propyl-3-(4-n-pentylphenyl)-2-propene, 1-acetoxy-2-iso-propyl-3-(4-n-hexylphenyl)-2-propene, 1-acetoxy-2-iso-propyl-3-(4-n-heptylphenyl)-2-propene, 1-acetoxy-2-iso-propyl-3-(4-n-octylphenyl)-2-propene, 1-acetoxy-2-iso-propyl-3-(4-n-nonylphenyl)-2-propene, 1-acetoxy-2-iso-propyl-3-(4-n-decylphenyl)-2-propene, 1-acetoxy-2-phenylmethyl-3-phenyl-2-propene, 1-acetoxy-2-phenylmethyl-3-(2-fluorophenyl)-2-propene, 1-acetoxy-2-phenylmethyl-3-(3-fluorophenyl)-2-propene, 1-acetoxy-2-phenylmethyl-3-(4-fluorophenyl)-2-propene, 1-acetoxy-2-phenylmethyl-3-(2-chlorophenyl)-2-propene, 1-acetoxy-2-phenylmethyl-3-(3-chlorophenyl)-2-propene, 1-acetoxy-2-phenylmethyl-3-(4-chlorophenyl)-2-propene, 1-acetoxy-2-phenylmethyl-3-(2-bromophenyl)-2-propene, 1-acetoxy-2-phenylmethyl-3-(3-bromophenyl)-2-propene, 1-acetoxy-2-phenylmethyl-3-(4-bromophenyl)-2-propene, 1-acetoxy-2-phenylmethyl-3-(2-methylphenyl)-2-propene, 1-acetoxy-2-phenylmethyl-3-(3-methylphenyl)-2-propene, 1-acetoxy-2-phenylmethyl-3-(4-methylphenyl)-2-propene, 1-acetoxy-2-phenylmethyl-3-(2-ethylphenyl)-2-propene, 1-acetoxy-2-phenylmethyl-3-(3-ethylphenyl)-2-propene, 1-acetoxy-2-phenylmethyl-3-(4-ethylphenyl)-2-propene, 1-acetoxy-2-phenylmethyl-3-(2-n-propylphenyl)-2-propene, 1-acetoxy-2-phenylmethyl-3-(3-n-propylphenyl)-2-propene, 1-acetoxy-2-phenylmethyl-3-(4-n-propylphenyl)-2-propene, 1-acetoxy-2-phenylmethyl-3-(2-iso-propylphenyl)-2-propene, 1-acetoxy-2-phenylmethyl-3-(3-iso-propylphenyl)-2-propene, 1-acetoxy-2-phenylmethyl-3-(4-iso-propylphenyl)-2-propene, 1-acetoxy-2-phenylmethyl-3-(2-n-butylphenyl)-2-propene, 1-acetoxy-2-phenylmethyl-3-(3-n-butylphenyl)-2-propene, 1-acetoxy-2-phenylmethyl-3-(4-n-butylphenyl)-2-propene, 1-acetoxy-2-phenylmethyl-3-(2-tert-butylphenyl)-2-propene, 1-acetoxy-2-phenylmethyl-3-(3-tert-butylphenyl)-2-propene, 1-acetoxy-2-phenylmethyl-3-(4-tert-butylphenyl)-2-propene, 1-acetoxy-2-phenylmethyl-3-(4-n-pentylphenyl)-2-propene, 1-acetoxy-2-phenylmethyl-3-(4-n-hexylphenyl)-2-propene, 1-acetoxy-2-phenylmethyl-3-(4-n-heptylphenyl)-2-propene, 1-acetoxy-2-phenylmethyl-3-(4-n-octylphenyl)-2-propene, 1-acetoxy-2-phenylmethyl-3-(4-n-nonylphenyl)-2-propene, 1-acetoxy-2-phenylmethyl-3-(4-n-decylphenyl)-2-propene, 1-acetoxy-3-(1-naphthyl)-2-propene, 1-acetoxy-3-(2-naphthyl)-2-propene, 1-acetoxy-2-methyl-3-(1-naphthyl)-2-propene, 1-acetoxy-2-methyl-3-(2-naphthyl)-2-propene, 1,1-diacetoxy-2-propene, 1,1-diacetoxy-2-butene, 1,1-diacetoxy-2-pentene, 1,1-diacetoxy-2-hexene, 1,1-diacetoxy-2-heptene, 1,1-diacetoxy-2-octene, 1,1-diacetoxy-2-nonene, 1,1-diacetoxy-2-decene, 1,1-diacetoxy-3-cyclohexyl-2-propene, 1,1-diacetoxy-2-methyl-2-propene, 1,1-diacetoxy-2-methyl-2-butene, 1,1-diacetoxy-2-methyl-2-pentene, 1,1-diacetoxy-2-methyl-2-hexene, 1,1-diacetoxy-2-methyl-2-heptene, 1,1-diacetoxy-2-methyl-2-octene, 1,1-diacetoxy-2-methyl-2-nonene, 1,1-diacetoxy-2-methyl-2-decene, 1,1-diacetoxy-2-ethyl-2-propene, 1,1-diacetoxy-2-ethyl-2-butene, 1,1-diacetoxy-2-ethyl-2-pentene, 1,1-diacetoxy-2-ethyl-2-hexene, 1,1-diacetoxy-2-ethyl-2-heptene, 1,1-diacetoxy-2-ethyl-2-octene, 1,1-diacetoxy-2-ethyl-2-nonene, 1,1-diacetoxy-2-ethyl-2-decene, 1,1-diacetoxy-3-cyclohexyl-2-ethyl-2-propene, 1,1-diacetoxy-2-n-propyl-2-propene, 1,1-diacetoxy-2-n-propyl-2-butene, 1,1-diacetoxy-2-n-propyl-2-pentene, 1,1-diacetoxy-2-n-propyl-2-hexene, 1,1-diacetoxy-2-n-propyl-2-heptene, 1,1-diacetoxy-2-n-propyl-2-octene, 1,1-diacetoxy-2-n-propyl-2-nonene, 1,1-diacetoxy-2-n-propyl-2-decene, 1,1-diacetoxy-3-cyclohexyl-2- n-propyl-2-propene, 1,1-diacetoxy-2-iso-propyl-2-propene, 1,1-diacetoxy-2-iso-propyl-2-butene, 1,1-diacetoxy-2-iso-propyl-2-pentene, 1,1-diacetoxy-2-iso-propyl-2-hexene, 1,1-diacetoxy-2-iso-propyl-2-heptene, 1,1-diacetoxy-2-iso-propyl-2-octene, 1,1-diacetoxy-2-iso-propyl-2-nonene, 1,1-diacetoxy-2-iso-propyl-2-decene, 1,1-diacetoxy-3-cyclohexyl-iso-propyl-2-propene, 1,1-diacetoxy-2-phenylmethyl-2-propene, 1,1-diacetoxy-2-phenylmethyl-2-butene, 1,1-diacetoxy-2-phenylmethyl-2-pentene, 1,1-diacetoxy-2-phenylmethyl-2-hexene, 1,1-diacetoxy-2-phenylmethyl-2-heptene, 1,1-diacetoxy-2-phenylmethyl-2-octene, 1,1-diacetoxy-2-phenylmethyl-2-nonene, 1,1-diacetoxy-2-phenylmethyl-2-decene, 1,1-diacetoxy-3-cyclohexyl-2-phenylmethyl-2-propene, 1,1-diacetoxy-3-phenyl-2-propene, 1,1-diacetoxy-3-(2-fluorophenyl)-2-propene, 1,1-diacetoxy-3-(3-fluorophenyl)-2-propene, 1,1-diacetoxy-3-(4-fluorophenyl)-2-propene, 1,1-diacetoxy-3-(2-chlorophenyl)-2-propene, 1,1-diacetoxy-3-(3-chlorophenyl)-2-propene, 1,1-diacetoxy-3-(4-chlorophenyl)-2-propene, 1,1-diacetoxy-3-(2-bromophenyl)-2-propene, 1,1-diacetoxy-3-(3-bromophenyl)-2-propene, 1,1-diacetoxy-3-(4-bromophenyl)-2-propene, 1,1-diacetoxy-3-(2-methylphenyl)-2-propene, 1,1-diacetoxy-3-(3-methylphenyl)-2-propene, 1,1-diacetoxy-3-(4-methylphenyl)-2-propene, 1,1-diacetoxy-3-(2-ethylphenyl)-2-propene, 1,1-diacetoxy-3-(3-ethylphenyl)-2-propene, 1,1-diacetoxy-3-(4-ethylphenyl)-2-propene, 1,1-diacetoxy-3-(2-n-propylphenyl)-2-propene, 1,1-diacetoxy-3-(3-n-propylphenyl)-2-propene, 1,1-diacetoxy-3-(4-n-propylphenyl)-2-propene, 1,1-diacetoxy-3-(2-iso-propylphenyl)-2-propene, 1,1-diacetoxy-3-(3-iso-propylphenyl)-2-propene, 1,1-diacetoxy-3-(4-iso-propylphenyl)-2-propene, 1,1-diacetoxy-3-(2-n-butylphenyl)-2-propene, 1,1-diacetoxy-3-(3-n-butylphenyl)-2-propene, 1,1-diacetoxy-3-(4-n-butylphenyl)-2-propene, 1,1-diacetoxy-3-(2-tert-butylphenyl)-2-propene; 1,1-diacetoxy-3-(3-tert-butylphenyl)-2-propene, 1,1-diacetoxy-3-(4-tert-butylphenyl)-2-propene, 1,1-diacetoxy-3-(4-n-pentylphenyl)-2-propene, 1,1-diacetoxy-3-(4-n-hexylphenyl)-2-propene, 1,1-diacetoxy-3-(4-n-heptylphenyl)-2-propene, 1,1-diacetoxy-3-(4-n-octylphenyl)-2-propene, 1,1-diacetoxy-3-(4-n-nonylphenyl)-2-propene, 1,1-diacetoxy-3-(4-n-decylphenyl)-2-propene, 1,1-diacetoxy-2-methyl-3-phenyl-2-propene, 1,1-diacetoxy-2-methyl-3-(2-fluorophenyl)-2-propene, 1,1-diacetoxy-2-methyl-3-(3-fluorophenyl)-2-propene, 1,1-diacetoxy-2-methyl-3-(4-fluorophenyl)-2-propene, 1,1-diacetoxy-2-methyl-3-(2-chlorophenyl)-2-propene, 1,1-diacetoxy-2-methyl-3-(3-chlorophenyl)-2-propene, 1,1-diacetoxy-2-methyl-3-(4-chlorophenyl)-2-propene, 1,1-diacetoxy-2-methyl-3-(2-bromophenyl)-2-propene, 1,1-diacetoxy-2-methyl-3-(3-bromophenyl)-2-propene, 1,1-diacetoxy-2-methyl-3-(4-bromophenyl)-2-propene, 1,1-diacetoxy-2-methyl-3-(2-methylphenyl)-2-propene, 1,1-diacetoxy-2-methyl-3-(3-methylphenyl)-2-propene, 1,1-diacetoxy-2-methyl-3-(4-methylphenyl)-2-propene, 1,1-diacetoxy-2-methyl-3-(2-ethylphenyl)-2-propene, 1,1-diacetoxy-2-methyl-3-(3-ethylphenyl)-2-propene, 1,1-diacetoxy-2-methyl-3-(4-ethylphenyl)-2-propene, 1,1-diacetoxy-2-methyl-3-(2-n-propylphenyl)-2-propene, 1,1-diacetoxy-2-methyl-3-(3-n-propylphenyl)-2-propene, 1,1-diacetoxy-2-methyl-3-(4-n-propylphenyl)-2-propene, 1,1-diacetoxy-2-methyl-3-(2-iso-propylphenyl)-2-propene, 1,1-diacetoxy-2-methyl-3-(3-iso-propylphenyl)-2-propene, 1,1-diacetoxy-2-methyl-3-(4-iso-propylphenyl)-2-propene, 1,1-diacetoxy-2-methyl-3-(2-n-butylphenyl)-2-propene, 1,1-diacetoxy-2-methyl-3-(3-n-butylphenyl)-2-propene, 1,1-diacetoxy-2-methyl-3-(4-n-butylphenyl)-2-propene, 1,1-diacetoxy-2-methyl-3-(2-tert-butylphenyl)-2-propene, 1,1-diacetoxy-2-methyl-3-(3-tert-butylphenyl)-2-propene, 1,1-diacetoxy-2-methyl-3-(4-tert-butylphenyl)-2-propene, 1,1-diacetoxy-2-methyl-3-(4-n-pentylphenyl)-2-propene, 1,1-diacetoxy-2-methyl-3-(4-n-hexylphenyl)-2-propene, 1,1-diacetoxy-2-methyl-3-(4-n-heptylphenyl)-2-propene, 1,1-diacetoxy-2-methyl-3-(4-n-octylphenyl)-2-propene, 1,1-diacetoxy-2-methyl-3-(4-n-nonylphenyl)-2-propene, 1,1-diacetoxy-2-methyl-3-(4-n-decylphenyl)-2-propene, 1,1-diacetoxy-2-ethyl-3-phenyl-2-propene, 1,1-diacetoxy-2-ethyl-3-(2-fluorophenyl)-2-propene, 1,1-diacetoxy-2-ethyl-3-(3-fluorophenyl)-2-propene, 1,1-diacetoxy-2-ethyl-3-(4-fluorophenyl)-2-propene, 1,1-diacetoxy-2-ethyl-3-(2-chlorophenyl)-2-propene, 1,1-diacetoxy-2-ethyl-3-(3-chlorophenyl)-2-propene, 1,1-diacetoxy-2-ethyl-3-(4-chlorophenyl)-2-propene, 1,1-diacetoxy-2-ethyl-3-(2-bromophenyl)-2-propene, 1,1-diacetoxy-2-ethyl-3-(3-bromophenyl)-2-propene, 1,1-diacetoxy-2-ethyl-3-(4-bromophenyl)-2-propene, 1,1-diacetoxy-2-ethyl-3-(2-methylphenyl)-2-propene, 1,1-diacetoxy-2-ethyl-3-(3-methylphenyl)-2-propene, 1,1-diacetoxy-2-ethyl-3-(4-methylphenyl)-2-propene, 1,1-diacetoxy-2-ethyl-3-(2-ethylphenyl)-2-propene, 1,1-diacetoxy-2-ethyl-3-(3-ethylphenyl)-2-propene, 1,1-diacetoxy-2-ethyl-3-(4-ethylphenyl)-2-propene, 1,1-diacetoxy-2-ethyl-3-(2-n-propylphenyl)-2-propene, 1,1-diacetoxy-2-ethyl-3-(3-n-propylphenyl)-2-propene. 1,1-diacetoxy-2-ethyl-3-(4-n-propylphenyl)-2-propene, 1,1-diacetoxy-2-ethyl-3-(2-iso-propylphenyl)-2-propene, 1,1-diacetoxy-2-ethyl-3-(3-iso-propylphenyl)-2-propene, 1,1-diacetoxy-2-ethyl-3-(4-iso-propylphenyl)-2-propene, 1,1-diacetoxy-2-ethyl-3-(2-n-butylphenyl)-2-propene, 1,1-diacetoxy-2-ethyl-3-(3-n-butylphenyl)-2-propene, 1,1-diacetoxy-2-ethyl-3-(4-n-butylphenyl)-2-propene, 1,1-diacetoxy-2-ethyl-3-(2-tert-butylphenyl)-2-propene, 1,1-diacetoxy-2-ethyl-3-(3-tert-butylphenyl)-2-propene, 1,1-diacetoxy-2-ethyl-3-(4-tert-butylphenyl)-2-propene, 1,1-diacetoxy-2-ethyl-3-(4-n-pentylphenyl)-2-propene, 1,1-diacetoxy-2-ethyl-3-(4-n-hexylphenyl)-2-propene, 1,1-diacetoxy-2-ethyl-3-(4-n-heptylphenyl)-2-propene, 1,1-diacetoxy-2-ethyl-3-(4-n-octylphenyl)-2-propene, 1,1-diacetoxy-2-ethyl-3-(4-n-nonylphenyl)-2-propene, 1,1-diacetoxy-2-ethyl-3-(4-n-decylphenyl)-2-propene, 1,1-diacetoxy-2-n-propyl-3-phenyl-2-propene, 1,1-diacetoxy-2-n-propyl-3-(2-fluorophenyl)-2-propene, 1,1-diacetoxy-2-n-propyl-3-(3-fluorophenyl)-2-propene, 1,1-diacetoxy-2-n-propyl-3-(4-fluorophenyl)-2-propene, 1,1-diacetoxy-2-n-propyl-3-(2-chlorophenyl)-2-propene, 1,1-diacetoxy-2-n-propyl-3-(3-chlorophenyl)-2-propene, 1,1-diacetoxy-2-n-propyl-3-(4-chlorophenyl)-2-propene, 1,1-diacetoxy-2-n-propyl-3-(2-bromophenyl)-2-propene, 1,1-diacetoxy-2-n-propyl-3-(3-bromophenyl)-2-propene, 1,1-diacetoxy-2-n-propyl-3-(4-bromophenyl)-2-propene, 1,1-diacetoxy-2-n-propyl-3-(2-methylphenyl)-2-propene, 1,1-diacetoxy-2-n-propyl-3-(3-methylphenyl)-2-propene, 1,1-diacetoxy-2-n-propyl-3-(4-methylphenyl)-2-propene, 1,1-diacetoxy-2-n-propyl-3-(2-ethylphenyl)-2-propene, 1,1-diacetoxy-2-n-propyl-3-(3-ethylphenyl)-2-propene, 1,1-diacetoxy-2-n-propyl-3-(4-ethylphenyl)-2-propene, 1,1-diacetoxy-2-n-propyl-3-(2-n-propylphenyl)-2-propene, 1,1-diacetoxy-2-n-propyl-3-(3-n-propylphenyl)-2-propene, 1,1-diacetoxy-2-n-propyl-3-(4-n-propylphenyl)-2-propene, 1,1-diacetoxy-2-n-propyl-3-(2-iso-propylphenyl)-2-propene, 1,1-diacetoxy-2-n-propyl-3-(3-iso-propylphenyl)-2-propene, 1,1-diacetoxy-2-n-propyl-3-(4-iso-propylphenyl)-2-propene, 1,1-diacetoxy-2-n-propyl-3-(2-n-butylphenyl)-2-propene, 1,1- diacetoxy-2-n-propyl-3-(3-n-butylphenyl)-2-propene, 1,1-diacetoxy-2-n-propyl-3-(4-n-butylphenyl)-2-propene, 1,1-diacetoxy-2-n-propyl-3-(2-tert-butylphenyl)-2-propene, 1,1-diacetoxy-2-n-propyl-3-(3-tert-butylphenyl)-2-propene, 1,1-diacetoxy-2-n-propyl-3-(4-tert-butylphenyl)-2-propene, 1,1-diacetoxy-2-n-propyl-3-(4-n-pentylphenyl)-2-propene, 1,1-diacetoxy-2-n-propyl-3-(4-n-hexylphenyl)-2-propene, 1,1-diacetoxy-2-n-propyl-3-(4-n-heptylphenyl)-2-propene, 1,1-diacetoxy-2-n-propyl-3-(4-n-octylphenyl)-2-propene, 1,1-diacetoxy-2-n-propyl-3-(4-n-nonylphenyl)-2-propene, 1,1-diacetoxy-2-n-propyl-3-(4-n-decylphenyl)-2-propene, 1,1-diacetoxy-2-iso-propyl-3-phenyl-2-propene, 1,1-diacetoxy-2-iso-propyl-3-(2-fluorophenyl)-2-propene, 1,1-diacetoxy-2-iso-propyl-3-(3-fluorophenyl)-2-propene, 1,1-diacetoxy-2-iso-propyl-3-(4-fluorophenyl)-2-propene, 1,1-diacetoxy-2-iso-propyl-3-(2-chlorophenyl)-2-propene, 1,1-diacetoxy-2-iso-propyl-3-(3-chlorophenyl)-2-propene, 1,1-diacetoxy-2-iso-propyl-3-(4-chlorophenyl)-2-propene, 1,1-diacetoxy-2-iso-propyl-3-(2-bromophenyl)-2-propene, 1,1-diacetoxy-2-iso-propyl-3-(3-bromophenyl)-2-propene, 1,1-diacetoxy-2-iso-propyl-3-(4-bromophenyl)-2-propene, 1,1-diacetoxy-2-iso-propyl-3-(2-methylphenyl)-2-propene, 1,1-diacetoxy-2-iso-propyl-3-(3-methylphenyl)-2-propene, 1,1-diacetoxy-2-iso-propyl-3-(4-methylphenyl)-2-propene, 1,1-diacetoxy-2-iso-propyl-3-(2-ethylphenyl)-2-propene, 1,1-diacetoxy-2-iso-propyl-3-(3-ethylphenyl)-2-propene, 1,1-diacetoxy-2-iso-propyl-3-(4-ethylphenyl)-2-propene, 1,1-diacetoxy-2-iso-propyl-3-(2-n-propylphenyl)-2-propene, 1,1-diacetoxy-2-iso-propyl-3-(3-n-propylphenyl)-2-propene, 1,1-diacetoxy-2-iso-propyl-3-(4-n-propylphenyl)-2-propene, 1,1-diacetoxy-2-iso-propyl-3-(2-iso-propylphenyl)-2-propene, 1,1-diacetoxy-2-iso-propyl-3-(3-iso-propylphenyl)-2-propene, 1,1-diacetoxy-2-iso-propyl-3-(4-iso-propylphenyl)-2-propene, 1,1-diacetoxy-2-iso-propyl-3-(2-n-butylphenyl)-2-propene, 1,1-diacetoxy-2-iso-propyl-3-(3-n-butylphenyl)-2-propene, 1,1-diacetoxy-2-iso-propyl-3-(4-n-butylphenyl)-2-propene, 1,1-diacetoxy-2-iso-propyl-3-(2-tert-butylphenyl)-2-propene, 1,1-diacetoxy-2-iso-propyl-3-(3-tert-butylphenyl)-2-propene, 1,1-diacetoxy-2-iso-propyl-3-(4-tert-butylphenyl)-2-propene, 1,1-diacetoxy-2-iso-propyl-3-(4-n-pentylphenyl)-2-propene, 1,1-diacetoxy-2-iso-propyl-3-(4-n-hexylphenyl)-2-propene, 1,1-diacetoxy-2-iso-propyl-3-(4-n-heptylphenyl)-2-propene, 1,1-diacetoxy-2-iso-propyl-3-(4-n-octylphenyl)-2-propene, 1,1-diacetoxy-2-iso-propyl-3-(4-n-nonylphenyl)-2-propene, 1,1-diacetoxy-2-iso-propyl-3-(4-n-decylphenyl)-2-propene, 1,1-diacetoxy-2-phenylmethyl-3-phenyl-2-propene, 1,1-diacetoxy-2-phenylmethyl-3-(2-fluorophenyl)-2-propene, 1,1-diacetoxy-2-phenylmethyl-3-(3-fluorophenyl)-2-propene, 1,1-diacetoxy-2-phenylmethyl-3-(4-fluorophenyl)-2-propene, 1,1-diacetoxy-2-phenylmethyl-3-(2-chlorophenyl)-2-propene, 1,1-diacetoxy-2-phenylmethyl-3-(3-chlorophenyl)-2-propene, 1,1-diacetoxy-2-phenylmethyl-3-(4-chlorophenyl)-2-propene, 1,1-diacetoxy-2-phenylmethyl-3-(2-bromophenyl)-2-propene, 1,1-diacetoxy-2-phenylmethyl-3-(3-bromophenyl)-2-propene, 1,1-diacetoxy-2-phenylmethyl-3-(4-bromophenyl)-2-propene, 1,1-diacetoxy-2-phenylmethyl-3-(2-methylphenyl)-2-propene, 1,1-diacetoxy-2-phenylmethyl-3-(3-methylphenyl)-2-propene, 1,1-diacetoxy-2-phenylmethyl-3-(4-methylphenyl)-2-propene, 1,1-diacetoxy-2-phenylmethyl-3-(2-ethylphenyl)-2-propene, 1,1-diacetoxy-2-phenylmethyl-3-(3-ethylphenyl)-2-propene, 1,1-diacetoxy-2-phenylmethyl-3-(4-ethylphenyl)-2-propene, 1,1-diacetoxy-2-phenylmethyl-3-(2-n-propylphenyl)-2-propene, 1,1-diacetoxy-2-phenylmethyl-3-(3-n-propylphenyl)-2-propene, 1,1-diacetoxy-2-phenylmethyl-3-(4-n-propylphenyl)-2-propene, 1,1-diacetoxy-2-phenylmethyl-3-(2-iso-propylphenyl)-2-propene, 1,1-diacetoxy-2-phenylmethyl-3-(3-iso-propylphenyl)-2-propene, 1,1-diacetoxy-2-phenylmethyl-3-(4-iso-propylphenyl)-2-propene, 1,1-diacetoxy-2-phenylmethyl-3-(2-n-butylphenyl)-2-propene, 1,1-diacetoxy-2-phenylmethyl-3-(3-n-butylphenyl)-2-propene, 1,1-diacetoxy-2-phenylmethyl-3-(4-n-butylphenyl)-2-propene, 1,1-diacetoxy-2-phenylmethyl-3-(2-tert-butylphenyl)-2-propene, 1,1-diacetoxy-2-phenylmethyl-3-(3-tert-butylphenyl)-2-propene, 1,1-diacetoxy-2-phenylmethyl-3-(4-tert-butylphenyl)-2-propene, 1,1-diacetoxy-2-phenylmethyl-3-(4-n-pentylphenyl)-2-propene, 1,1-diacetoxy-2-phenylmethyl-3-(4-n-hexylphenyl)-2-propene, 1,1-diacetoxy-2-phenylmethyl-3-(4-n-heptylphenyl)-2-propene, 1,1-diacetoxy-2-phenylmethyl-3-(4-n-octylphenyl)-2-propene, 1,1-diacetoxy-2-phenylmethyl-3-(4-n-nonylphenyl)-2-propene, 1,1-diacetoxy-2-phenylmethyl-3-(4-n-decylphenyl)-2-propene, 1,1-diacetoxy-3-(1-naphthyl)-2-propene, 1,1-diacetoxy-3-(2-naphthyl)-2-propene, 1,1-diacetoxy-2-methyl-3-(1-naphthyl)-2-propene, and 1,1-diacetoxy-2-methyl-3-(2-naphthyl)-2-propene.

In the reaction of the 2-fluoro-1,3-benzodithiol 1,1,3,3-tetraoxide derivative represented by the general formula (1) according to the present invention and allyl acetate, 0.8 to 1.5 moles of the 2-fluoro-1,3-benzodithiol 1,1,3,3-tetraoxide derivative represented by the general formula (1) is used with respect to the allyl acetate used in the reaction.

Metal catalysts that can be used in the reaction between the 2-fluoro-1,3-benzodithiol 1,1,3,3-tetraoxide derivative represented by the general formula (1) according to the present invention and allyl acetate include a metal catalyst capable of forming a π-allyl complex. Specific examples thereof include palladium(II) acetate, palladium(II) chloride, 1,2-phenylsulfinyl ethanepalladium(II) diacetate, allylpalladium(II) chloride (dimer), benzyl-bis-(triphenylphosphine)palladium (II) chloride, bis(2,4-pentanedionato)palladium(II), bis(acetonitrile)palladium(II) dichloride, bis(benzonitrile)palladium(II) dichloride, bis(ethylenediamine)palladium(II) dichloride, bis(methyldiphenylphosphine)palladium(II) dichloride, tetrakis(triphenylphosphine)palladium(II) dichloride, bis(dibenzylideneacetone)palladium(0), bis(tri-tert-butylphosphine)palladium(0), and tetrakis(triphenylphosphine)palladium(0). The used amount of the metal catalyst is 0.001 to 0.5 moles with respect to the allyl acetate used in the reaction.

Examples of bases that can be used in the reaction between the 2-fluoro-1,3-benzodithiol 1,1,3,3-tetraoxide derivative represented by the general formula (1) according to the present invention and allyl acetate include lithium carbonate, sodium carbonate, potassium carbonate, triethylamine, 4-dimethylaminopyridine, 1,5-diazabicyclo[4.3.0]-5-nonene, 1,8-diazabicyclo[5.4.0]-7-undecene, 1,4-diazabicyclo[2,2,2]octane, sodium hydride, potassium hydride, sodium methoxide, potassium methoxide, sodium ethoxide, potassium ethoxide, sodium tert-butoxide, and potassium tert-butoxide. The used amount of the base is 0.9 to 1.5 moles with respect to the 2-fluoro-1,3-benzodithiol 1,1,3,3-tetraoxide derivative represented by the general formula (1) used in the reaction.

As solvents that can be used in the reaction between the 2-fluoro-1,3-benzodithiol 1,1,3,3-tetraoxide derivative represented by the general formula (1) according to the present invention and allyl acetate, any solvent may be used as long as it is inert in the reaction. Specific examples thereof include halogenated hydrocarbons such as dichloromethane and chloroform, ethers such as diethyl ether, di-iso-propyl ether, and tetrahydrofuran, and aromatic hydrocarbons such as benzene, toluene, and xylene. The used amount of the solvent is 5 to 100 times by weight the 2-fluoro-1,3-benzodithiol 1,1,3,3-tetraoxide derivative represented by the general formula (1) used in the reaction.

Although the temperature and time in the reaction between the 2-fluoro-1,3-benzodithiol 1,1,3,3-tetraoxide derivative represented by the general formula (1) according to the present invention and allyl acetate depend on the type of 2-fluoro-1,3-benzodithiol 1,1,3,3-tetraoxide derivative represented by the general formula (1) that is used, the type of allyl acetate, the type of catalyst, and the type of used solvent, generally, the reaction is completed by reacting for 1 to 48 hours in a temperature range of 0 to 80° C.

The reaction between the 2-fluoro-1,3-benzodithiol 1,1,3,3-tetraoxide derivative represented by the general formula (1) according to the present invention and a diallyl acetate may be an asymmetric reaction. In such a case, an optically active ligand is used. Specific examples of chiral ligands that can be used include, but are not limited to, (R)-(+)-2,2'-bis(diphenylphospino)-1,1'-binaphthyl (hereinafter, abbreviated as (R)-(+)-BINAP), (R)-(+)-2-diphenylphospino-2'-methoxy-1,1'-binaphthyl, and (R)-(+)-2,2'-dimethoxy-6,6'-bis(diphenylphospino)-1,1'-biphenyl. The used amount of this optically active ligand is 0.9 to 1.5 moles with respect to the used metal catalyst. The structure of the obtained product is an (S) isomer. If the enantiomers (S)-(−)-2,2'-bis(diphenylphospino)-1,1'-binaphthyl, (S)-(−)-2-diphenylphospino-2'-methoxy-1,1'-binaphthyl, (S)-(−)-2,2'-dimethoxy-6,6'-bis(diphenylphospino)-1,1'-biphenyl and the like are used as the optically active ligand, the obtained product is the (R) isomer.

Specific examples of carbonyl group-containing compounds for which the 2-fluoro-1,3-benzodithiol 1,1,3,3-tetraoxide derivative represented by the general formula (1) according to the present invention can be used as the introduction agent for a monofluoromethyl group precursor include, but are not limited to, acetaldehyde, n-propioaldehyde, n-butylaldehyde, n-pentylaldehyde, n-hexylaldehyde, n-heptylaldehyde, n-octylaldehyde, n-nonylaldehyde, n-decylaldehyde, cyclohexylaldehyde, benzaldehyde, 2-fluorobenzaldehyde, 3-fluorobenzaldehyde, 4-fluorobenzaldehyde, 2-chlorobenzaldehyde, 3-chlorobenzaldehyde, 4-chlorobenzaldehyde, 2-bromobenzaldehyde, 3-bromobenzaldehyde, 4-bromobenzaldehyde, 2-methylbenzaldehyde, 3-methylbenzaldehyde, 4-methylbenzaldehyde, 2-ethylbenzaldehyde, 3-ethylbenzaldehyde, 4-ethylbenzaldehyde, 2-n-propylbenzaldehyde, 3-n-propylbenzaldehyde, 4-n-propylbenzaldehyde, 2-iso-propylbenzaldehyde, 3-iso-propylbenzaldehyde, 4-iso-propylbenzaldehyde, 2-n-butylbenzaldehyde, 3-n-butylbenzaldehyde, 4-n-butylbenzaldehyde, 2-tert-butylbenzaldehyde, 3-tert-butylbenzaldehyde, 4-tert-butylbenzaldehyde, 2-n-pentylbenzaldehyde, 3-n-pentylbenzaldehyde, 4-n-pentylbenzaldehyde, 4-n-hexylbenzaldehyde, 4-n-heptylbenzaldehyde, 4-n-octylbenzaldehyde, 4-n-nonylbenzaldehyde, 4-n-decylbenzaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 2-n-propoxybenzaldehyde, 3-n-propoxybenzaldehyde, 4-n-propoxybenzaldehyde, 2-isopropoxybenzaldehyde, 3-iso-propoxybenzaldehyde, 4-iso-propoxybenzaldehyde. 2-n-butoxybenzaldehyde, 3-n-butoxybenzaldehyde, 4-n-butoxybenzaldehyde, 2-tert-butoxybenzaldehyde, 3-tert-butoxybenzaldehyde, 4-tert-butoxybenzaldehyde, 2-n-pentoxybenzaldehyde, 3-n-pentoxybenzaldehyde, 4-n-pentoxybenzaldehyde, 4-n-hexyloxybenzaldehyde, 4-n-heptyloxybenzaldehyde, 4-n-octyloxybenzaldehyde, 4-n-nonyloxybenzaldehyde, 4-n-decyloxybenzaldehyde, cinnamaldehyde, 4-methylcinnamaldehyde, 4-ethylcinnamaldehyde, 4-n-propylcinnamaldehyde, 4-iso-propylcinnamaldehyde, 4-n-butylcinnamaldehyde, 4-tert-butylcinnamaldehyde, 4-n-pentylcinnamaldehyde, 4-n-hexylcinnamaldehyde, 4-n-heptylcinnamaldehyde, 4-n-octylcinnamaldehyde, 4-n-nonylcinnamaldehyde, 4-n-decylcinnamaldehyde, 4-methoxycinnamaldehyde, 4-ethoxycinnamaldehyde, 4-n-propoxycinnamaldehyde, 4-iso-propoxycinnamaldehyde, 4-n-butoxycinnamaldehyde, 4-tert-butoxycinnamaldehyde, 4-n-pentyloxycinnamaldehyde, 4-n-hexyloxycinnamaldehyde, 4-n-heptyloxycinnamaldehyde, 4-n-octyloxycinnamaldehyde, 4-n-nonyloxycinnamaldehyde, 4-n-decyloxycinnamaldehyde, 2-fluorocinnamaldehyde, 3-fluorocinnamaldehyde, 5-fluorocinnamaldehyde, 2-chlorocinnamaldehyde, 3-chlorocinnamaldehyde, 5-chlorocinnamaldehyde, 2-bromocinnamaldehyde, 3-bromocinnamaldehyde, 5-bromocinnamaldehyde, acetone, butan-2-one, pentan-2-one, hexan-2-one, heptan-2-one, octan-2-one, nonan-2-one, decan-2-one, acetophenone, 2-fluoroacetophenone, 3-fluoroacetophenone, 4-fluoroacetophenone, 2-chloroacetophenone, 3-chloroacetophenone, 4-chloroacetophenone, 2-bromoacetophenone, 3-bromoacetophenone, 4-bromoacetophenone, 4-methylacetophenone, 4-ethylacetophenone, 4-n-propylacetophenone, 4-iso-propylacetophenone, 4-n-butylacetophenone, 4-tert-butylacetophenone, 4-n-pentylacetophenone, 4-n-hexylacetophenone, 4-n-heptylacetophenone, 4-n-octylacetophenone, 4-n-nonylacetophenone, 4-n-decylacetophenone, 4-methoxy acetophenone, 4-ethoxyacetophenone, 4-n-propoxyacetophenone, 4-iso-propoxyacetophenone, 4-n-butoxyacetophenone, 4-tert-butoxyacetophenone, 4-n-pentyloxyacetophenone, 4-n-hexyloxyacetophenone, 4-n-heptyloxyacetophenone, 4-n-octyloxyacetophenone, 4-n-nonyloxyacetophenone, 4-n-decyloxyacetophenone, (1-naphtho)phenone, (2-naphtho)phenone, and benzophenone.

In the reaction between the 2-fluoro-1,3-benzodithiol 1,1,3,3-tetraoxide derivative represented by the general formula (1) according to the present invention and the carbonyl group-containing compound, the used amount of the 2-fluoro-1,3-benzodithiol 1,1,3,3-tetraoxide derivative represented by the general formula (1) is 0.8 to 2.0 moles with respect to the carbonyl group-containing compound.

The reaction for obtaining an adduct represented by the general formula (6) from the reaction between the 2-fluoro-1,3-benzodithiol 1,1,3,3-tetraoxide derivative represented by the general formula (1) according to the present invention and the carbonyl group-containing compound can be carried out in a reaction-inert organic solvent in the presence of a base.

Specific examples of bases that can be used in the reaction for obtaining the adduct represented by the general formula (6) from the reaction between the 2-fluoro-1,3-benzodithiol 1,1,3,3-tetraoxide derivative represented by the general formula (1) according to the present invention and the carbonyl group-containing compound include, but are not limited to, triethylamine, 4-dimethylaminopyridine, 1,5-diazabicyclo[4.3.0]-5-nonene, 1,8-diazabicyclo[5.4.0]-7-undecene, 1,4-diazabicyclo[2,2,2]octane, sodium hydride, potassium hydride, sodium methoxide, potassium methoxide, sodium ethoxide, potassium ethoxide, sodium tert-butoxide, and potassium tert-butoxide. The used amount of the base is 0.9 to 1.5 moles with respect to the 2-fluoro-1,3-benzodithiol 1,1,3,3-tetraoxide derivative represented by the general formula (1) used in the reaction. Further, to inhibit the reverse reaction, 0.9 to 1.5 moles of trimethylsilyl chloride may also be added.

Specific examples of solvents that can be used in the reaction for obtaining the adduct represented by the general formula (6) from the reaction between the 2-fluoro-1,3-benzodithiol 1,1,3,3-tetraoxide derivative represented by the general formula (1) according to the present invention and the carbonyl group-containing compound include, but are not limited to, halogenated hydrocarbons such as dichloromethane and chloroform, ethers such as diethyl ether, di-iso-propyl ether, and tetrahydrofuran, and aromatic hydrocarbons such as benzene, toluene, and xylene. The used amount of the solvent is 5 to 100 times by weight the 2-fluoro-1,3-benzodithiol 1,1,3,3-tetraoxide derivative represented by the general formula (1) used in the reaction.

Although the reaction temperature and time for obtaining the adduct represented by the general formula (6) from the reaction between the 2-fluoro-1,3-benzodithiol 1,1,3,3-tetraoxide derivative represented by the general formula (1) according to the present invention and the carbonyl group-containing compound depend on the type of substrate used in the reaction, the type of solvent, and the used base, the reaction is completed in 1 to 48 hours in a temperature range of 0 to 80° C.

In the derivation to a monofluoromethyl group-containing compound from the 2-substituted-2-fluoro-1,3-benzodithiol 1,1,3,3-tetraoxide derivative represented by the general formulae (4), (7), and (11) according to the present invention, desulfonation can be carried out by performing a reduction reaction.

Examples of reduction methods that can be used in the derivation to a monofluoromethyl group-containing compound from the 2-substituted-2-fluoro-1,3-benzodithiol 1,1,3,3-tetraoxide derivative represented by the general formulae (4), (7), and (11) according to the present invention include catalytic hydrogenation using a palladium metal catalyst and the like, reduction with a metal such as lithium, sodium, potassium, and magnesium, and reduction with a reducing agent, such as sodium hydride, lithium aluminumhydride, and samarium (II) iodide. Catalytic hydrogenation with a palladium metal catalyst and the like is carried out on the substrate used in the reaction using excess hydrogen under normal or increased pressure using 0.001 to 0.5 moles of the palladium metal catalyst and the like. In the case of reduction with a metal or with a reducing agent, the used amount of the metal or reducing agent is 1 to 20 moles with respect to the 2-substituted-2-fluoro-1,3-benzodithiol 1,1,3,3-tetraoxide derivative used in the reaction.

Solvents that can be used in the reduction reaction for the derivation to a monofluoromethyl group-containing compound from the 2-substituted-2-fluoro-1,3-benzodithiol 1,1,3,3-tetraoxide derivative represented by the general formulae (4), (7), and (11) according to the present invention are not especially limited as long as the solvent is inert in the reaction. The solvent depends on the type of palladium metal catalyst and the like, metal, or reducing agent that is used. For example, when using a palladium metal catalyst and the like, examples of the solvent include acetic acid and methanol. When using lithium, sodium, potassium, magnesium, sodium hydride, lithium aluminum hydride and the like, examples of the solvent include an ether solvent, such as diethylether and tetrahydrofuran. When using samarium(II) iodide and the like, examples of the solvent include an alcohol solvent, such as methanol and ethanol. The used amount of solvent is 5 to 200 times by weight with respect to the 2-substituted-2-fluoro-1,3-benzodithiol 1,1,3,3-tetraoxide derivative used in the reaction.

Although the reaction temperature and time in the reduction reaction for the derivation to a monofluoromethyl group-containing compound from the 2-substituted-2-fluoro-1,3-benzodithiol 1,1,3,3-tetraoxide derivative represented by the general formulae (4), (7), and (11) according to the present invention depend on differences in the used reduction method, generally, the target product can be obtained by reacting for 0.1 to 24 hours in a temperature range of −80 to 80° C.

In the derivation to a monofluoromethyl group-containing compound from the 2-substituted-2-fluoro-1,3-benzodithiol 1,1,3,3-tetraoxide derivative represented by the general formulae (4), (7), and (11) according to the present invention, if hydrolyzing a compound having an ester group, this may be carried out either before or after the reduction reaction. However, from the perspective of stability of the product, it is preferred to carry out the reduction reaction after hydrolysis. Hydrolysis of the ester group may be carried out using a large excess of hydrochloric acid or sulfuric acid in an alcohol solvent such as methanol for 10 to 48 hours in a temperature range of 50 to 100° C. Further, the hydrolysis may be carried out using an aqueous alcohol solvent with an alkali metal hydroxide, such as lithium hydroxide and sodium hydroxide. If using an alkali metal hydroxide, the used amount of alkali metal hydroxide is 1.2 to 3.0 moles with respect to the 2-substituted-2-fluoro-1,3-benzodithiol 1,1,3,3-tetraoxide derivative used in the reaction. The target product can be obtained by reacting for 0.5 to 8 hours in a temperature range of −10 to 60° C. The amount of solvent used in the hydrolysis is 5 to 100 times by weight with respect to the 2-substituted-2-fluoro-1,3-benzodithiol 1,1,3,3-tetraoxide derivative used in the reaction.

The compounds represented by the general formulae (1), (4), (5), (6), (7), (8), (9), (11), (12), and (13) according to the present invention can, after the reaction has finished, be isolated by a common post-processing operation, or purified by silica gel column chromatography to obtain a high-purity product.

EXAMPLES

The present invention will now be described in more detail based on the following examples. However, the present invention is not limited to only these examples.

Reference Example 1

Preparation of 1,2-benzenedithiol

[Formula 14]

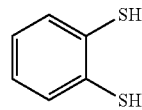

N,N,N,N-tetramethyl-1,2-ethylenediamine (30 ml, 0.2 mol) and n-butyl lithium (1.6 M, 250 ml, 2.2 mol) were weighed into a 500-ml eggplant-shaped flask provided with a stirrer, and the flask was then purged with argon. 91 ml of hexane was added to the mixture, and then the reaction mixture was ice-cooled to 0° C. Next, thiophenol (18.7 ml, 0.182 mol) was added to the mixture, and then the reaction mixture was stirred under ice-cooling for 1 hour. Then, the temperature was increased to room temperature, and the mixture was stirred for a further 12 hours. The mixture was again cooled to −20° C., and then well crushed sulfur powder (5.84 g, 0.182 mol) was added thereto. The mixture was stirred for 2 hours, and then the temperature was increased to room temperature. Next, the mixture was stirred for 12 hours. After the reaction finished, cooled 3 N hydrochloric acid was added to the reaction solution until the pH reached approximately 2. The hexane layer was separated, and the aqueous layer was extracted with diethylether. The obtained organic layer was collected, and the solvent was removed by distillation under reduced pressure to obtain the target product (16.783 g, yield 65%).

$^1$H-NMR (200 MHz; CDCl$_3$): δ 3.71 (2H, s, SH*2), 7.02-7.07 (2H, m, Ar), 7.32-7.36 (2H, m, Ar)

b.p.: 68-72° C. (180 Pa)

Reference Example 2

Preparation of 1,3-benzenedithiol

[Formula 15]

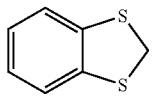

A 500-ml eggplant-shaped flask provided with a stirrer was charged with the dithiol prepared in Reference Example 1'(14.3 g, 101 mmol), potassium carbonate (20.8 g, 151 mmol), and N,N-dimethylformamide (200 ml), and the resultant mixture was dissolved at room temperature. Then, bromochloromethane (9.8 ml, 151 mmol) was slowly added dropwise. Next, the mixture was heated, and stirred for 3 hours at 110° C. After the reaction finished, water was added. The aqueous layer was extracted with diethylether and methylene chloride, then concentrated under reduced pressure to obtain the target product (12.5 g, yield 81%).

$^1$H-NMR (200 MHz; CDCl$_3$): δ 4.47 (2H, s, CH$_2$), 6.97-7.03 (2H, m, Ar), 7.16-7.24 (2H, m, Ar)

b.p.: 97.5-98.5° C. (290 Pa)

Reference Example 3

Preparation of 1,3-benzodithiol 1,1,3,3-tetraoxide

[Formula 16]

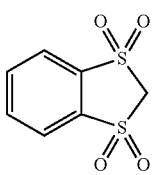

A 500-ml eggplant-shaped flask provided with a stirrer was charged with the 1,3-benzodithiol prepared in Reference Example 2 (12.5 g, 81.0 mmol) 130 ml of acetic acid, and 58 ml of 35% hydrogen peroxide aqueous solution, and the resultant mixture was stirred for 2 hours at room temperature. Then, the temperature was increased to 50° C., and the mixture was allowed to react overnight at that temperature. After the reaction finished, the temperature was cooled to 0° C. The deposited precipitate was collected by filtration, and then washed with water to obtain the target product (13.8 g, yield 86%) as a white solid.

$^1$H-NMR (200 MHz; CDCl$_2$): δ 4.70 (2H, s, CH$_2$), 7.90-8.03 (4H, m, Ar)

Example 1

Preparation of 2-fluoro-1,3-benzodithiol 1,1,3,3-tetraoxide

[Formula 17]

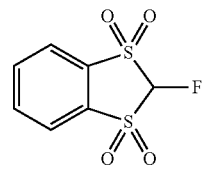

A 50 ml eggplant-shaped flask provided with a stirrer was charged with sodium hydride NaH (60% oil dispersion, 81.6 mg, 2.04 mmol) and 7.5 ml of tetrahydrofuran, and the resultant mixture was cooled to 0° C. Then, the 1,3-benzodithiol 1,1,3,3-tetraoxyoxide (445 mg, 2.04 mmol) obtained in Reference Example 3 was added, and the mixture was stirred at room temperature for 30 minutes to obtain a sodium salt suspension of 1,3-benzodithiol 1,1,3,3-tetraoxyoxide.

A separately prepared 50 ml eggplant-shaped flask provided with a stirrer was charged with N-fluoro-N'-(chloromethyl)triethylenediamine bis(tetrafluoroborate) (Selectfluor, 723 mg, 2.04 mmol) and acetonitrile (8 ml), and the resultant mixture was cooled to 0° C. Next, the above-prepared sodium salt suspension of 1,3-benzodithiol 1,1,3,3-tetraoxyoxide was added dropwise, and the mixture was then reacted for 3 hours at room temperature. After the reaction finished, water was added, and hydrogen was extracted with methylene chloride. The product was dried over anhydrous sodium sulfate, filtered, concentrated, and then purified by column chromatography (hexane:methylene chloride=2:8) to obtain a white substance (191 mg, yield 40%).

$^1$H-NMR (200 MHz; CDCl$_3$): δ 5.91 (1H, d, J=51.6 Hz, CH), 7.96-8.08 (4H, m, Ar)

$^{19}$F-NMR (188 MHz; CDCl$_3$): δ −165.3 (d, J=51.3 Hz)

MS: 235 (235.96) negative

Example 2

Preparation of 2-fluoro-2-[1-acetoxy-3-(2-naphthyl)-2-propenyl]-1,3-benzodithiol 1,1,3,3-tetraoxide

[Formula 18]

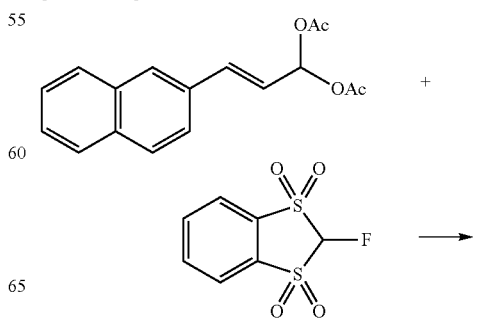

-continued

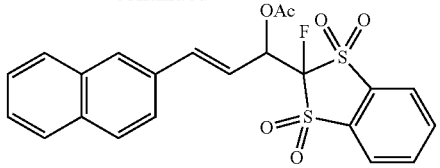

A 5 ml round-bottomed flask provided with a stirrer was charged with 3,3-diacetoxy-1-(2-naphthyl)-1-propene (242 mg, 0.85 mol) prepared based on the method described in J. Am. Chem. Soc., 2001, 123 (16), 3671-3686, allylpalladium (II) chloride (dimer) ([Pd(C$_3$H$_5$)Cl]$_2$, 23.4 mg, 0.064 mmol), and dichloromethane (0.85 ml), and the resultant mixture was stirred for 5 minutes at room temperature. Then, the mixture was charged with the cyclic monofluoro methylating agent (222 mg, 0.94 mmol) prepared in Working Example 1 and potassium carbonate (345 mg, 2.56 mmol), and reacted for 20 hours at room temperature. After the reaction finished, a saturated ammonium chloride aqueous solution was added. The aqueous layer was extracted with dichloromethane. The organic layers were combined and dried over anhydrous sodium sulfate, filtered, concentrated, and then purified by silica gel column chromatography (hexane:ethyl acetate=7:3) to obtain the target 2-fluoro-2-[1-acetoxy-3-(2-naphthyl)-2-propenyl]-1,3-benzodithiol 1,1,3,3-tetraoxide (239 mg, 0.52 mmol, yield 61%).

$^1$H-NMR (CDCl$_3$, 200 MHz) δ: 2.24 (s, 3H), 6.36 (dd, J=8.4, 15.8 Hz, 1H), 6.74 (dd, J=8.6, 25 Hz, 1H), 7.27 (d, J=15.6 Hz, 1H), 7.45-7.85 (m, 7H), 7.92-8.08 (m, 4H)

$^{19}$F-NMR (CDCl$_3$, 188 MHz) δ: −160.28 (d, J=25.2 Hz, 1F)

Examples 3 to 6

Using the same reaction apparatus as in Example 2, the target 2-substituted-2-fluoro-1,3-benzodithiol 1,1,3,3-tetraoxide derivative was obtained by performing the same operations as in Example 2, except that the 3,3-diacetoxy-1-(2-naphthyl)-1-propene was changed to the compound shown in Table 1 prepared by the same method. The results are shown in Table 1.

TABLE 1

| Example | Raw Material | Product | Yield (%) | Physical Property Values |
|---------|--------------|---------|-----------|--------------------------|
| Example 3 | (4-Cl-C₆H₄-CH=CH-CH(OAc)₂) | (fluorobenzodithiol tetraoxide product) | 52 | $^1$H-NMR (CDCl$_3$, 200 MHz) δ: 2.22 (s,, 3 H), 6.216 (dd, J = 8.4, 15.8 Hz, 1 H), 6.67 (dd, J = 8.4, 25.2 Hz, 1 H), 7.06 (d, J = 15.6 Hz, 1 H), 7.32 (d, J = 8.8 Hz, 2 H), 7.40 (d, J = 8.4 Hz, 2 H), 7.93-8.06 (m, 4 H) $^{19}$F-NMR (CDCl$_3$, 188 MHz) δ: −160.34 (d, J = 25.2 Hz, 1 F). |
| Example 4 | (4-Me-C₆H₄-CH=CH-CH(OAc)₂) | (fluorobenzodithiol tetraoxide product) | 46 | $^1$H-NMR (CDCl$_3$, 200 MHz) δ: 2.21 (s, 3 H), 2.35 (s, 3 H), 6.18 (dd, J = 8.6, 15.8 Hz, 1 H), 6.67 (dd, J = 8.5, 25.3 Hz, 1 H), 7.07 (d, J = 15.8 Hz, 1 H), 7.15 (d, J = 8.0 Hz, 2 H), 7.36 (d, J = 8.2 Hz, 2 H), 7.91-8.06 (m, 4 H). $^{19}$F-NMR (CDCl$_3$, 188 MHz) δ: −160.65 (d, J = 24. 8 Hz, 1 F). |
| Example 5 | (3-Cl-C₆H₄-CH=CH-CH(OAc)₂) | (fluorobenzodithiol tetraoxide product) | 72 | $^1$H-NMR (CDCl$_3$, 200 MHz) δ: 2.22 (s,, 3 H), 6.24 (dd, J = 8.0, 16.0 Hz, 1 H), 6.67 (dd, J = 8.6, 23.9 Hz, 1 H), 7.05 (d, J = 16.0 Hz, 1 H), 7.26-7.34 (m, 3 H), 7.46 (s, 1 H), 7.93-8.08 (m, 4 H). $^{19}$F-NMR (CDCl$_3$, 188 MHz) δ: −160.61 (d, J = 25.0 Hz, 1 F). |
| Example 6 | (Ph-CH=C(Me)-CH(OAc)₂) | (fluorobenzodithiol tetraoxide product) | 59 | $^1$H-NMR (CDCl$_3$, 200 MHz) δ: 2.07 (dd, J = 1.4, 3.0 Hz, 3 H), 2.25 (s, 3 H), 6.62 (d, J = 27.4 Hz, 1 H), 7.04 (s, 1 H), 7.26-7.36 (m, 5 H), 7.36 (d, J = 8.2 Hz, 2 H), 7.92-8.08 (m, 4 H). $^{19}$F-NMR (CDCl$_3$, 188 MHz) δ: −158.15 (d, J = 27.4 Hz, 1 F). |

Example 7

Preparation of 2-fluoro-2-(phenylhydroxymethyl)-1,3-benzodithiol 1,1,3,3-tetraoxide

[Formula 19]

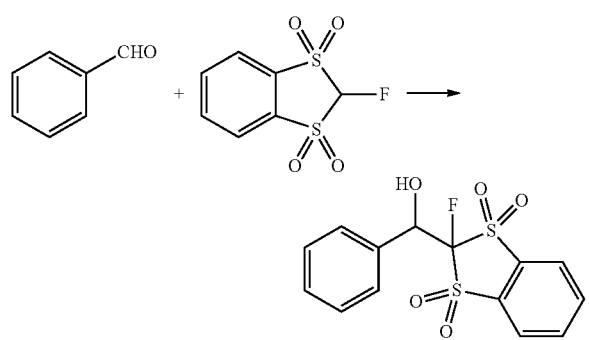

A 5 ml round-bottomed flask provided with a stirrer was charged with a cyclic monofluoro methylating reagent (23.6 mg, 0100 mmol), methylene chloride (0.3 ml), benzaldehyde (12 μm, 0.119 mmol), trimethylsilyl chloride (12.6 μm, 0.100 mmol), and 1,4-diazabicyclo[2,2,2]octane (DABCO, 22.4 mg, 0.200 mmol), and the resultant mixture was reacted for 24 hours at room temperature. After the reaction was finished, 6 N HCl was added, and the mixture was stirred for 30 minutes. The aqueous layer was then extracted with methylene chloride. The organic layers were combined and dried over sodium sulfate, filtered, concentrated, and then purified by silica gel column chromatography to obtain the target 2-(phenylhydroxymethyl)-1,3-benzodithiol 1,1,3,3-tetraoxide (27.1 mg, 0.079 mmol, yield 80%).

White solid $^1$H-NMR (200 MHz, CDCl$_3$): δ=6.11 (d, J=25.2 Hz, 1H), 7.25-7.50 (m, 3H), 7.64-7.67 (m, 2H), 7.90-8.00 (m, 3H), 8.07-8.11 (m, 1H)

$^{19}$F-NMR (188 MHz, CDCl$_3$): δ=164.0 (d, J=25.2 Hz, 1F)

Example 8

Preparation of 2-fluoro-2-(1-hydroxy-3-phenyl-2-propenyl)-1,3-benzodithiol 1,1,3,3-tetraoxide Using the same reaction apparatus as in Example 2, the target 2-fluoro-2-(1-hydroxy-3-phenyl-2-propenyl)-1,3-benzodithiol 1,1,3,3-tetraoxide (21.9 mg, 0.059 mmol, yield 60%) was obtained by performing the same operations as in Example 2, except that the benzaldehyde to the cinnamaldehyde.

White solid $^1$H-NMR (200 MHz, CDCl$_3$) δ=2.78 (br., 1H), 5.71 (dd, J=7.9, 23.9 Hz, 1H), 6.37 (dd, J=7.5, 15.7 Hz, 1H), 7.03 (d, J=16.0 Hz, 1H), 7.30-7.50 (m, 5H), 7.91-8.10 (m, 4H)

$^{19}$F-NMR (188 MHz, CDCl$_3$) δ=−164.7 (d, J=23.3 Hz, 1F)

Example 9

Preparation of (E)-1-fluoro-4-phenyl-3-buten-2-ol

[Formula 20]

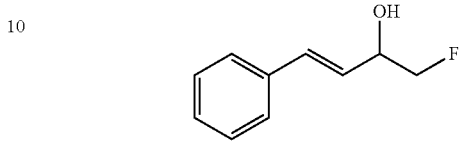

A 5 ml round-bottomed flask provided with a stirrer was purged with nitrogen, and then methanol (2.0 ml) which had been frozen and deaerated was added to the 2-fluoro-2-(phenylhydroxymethyl)-1,3-benzodithiol 1,1,3,3-tetraoxide (41.2 mg, 0.11 mmol) obtained in Example 8. The resultant mixture was cooled to −60° C., then samarium(II) iodide/tetrahydrofuran (0.1 M, 6.7 ml) was added dropwise, and the mixture was stirred for 1 hour while increasing the temperature to −40° C. A saturated ammonium chloride aqueous solution and sodium hyposulfite was added to the mixture, and the insoluble matter was filtered off. The aqueous layer was then extracted with ethyl acetate, then the organic layer was dried over anhydrous sodium sulfate. The solvent was removed by distillation using an evaporator. The resultant product was purified by silica gel column chromatography (hexane:ethyl acetate=7:3) to obtain 3 (14.8 mg, yield 81%). Molecular weight: 166.19

$^1$H NMR (CDCl$_3$, 200 MHz) δ: 2.51 (brs., 1H), 4.35 (ddd, J=47.6, 9.6, 7.2 Hz, 1H), 4.46 (ddd, J=47.0, 9.4, 3.4 Hz, 1H), 4.47-4.70 (brm., 1H), 6.15 (dd, J=16.0, 6.0 Hz, 1H), 6.74 (d, J=16.2 Hz, 1H)

$^{13}$C NMR (CDCl$_3$, 150.9 MHz) δ: 71.8 (d, J=20.2 Hz), 86.4 (d, J=173.5 Hz), 125.7 (d, J=8.1 Hz), 126.9, 128.4, 129.0, 133.4, 136.4

$^{19}$F NMR (CDCl$_3$, 188 MHz) δ: −224.4 (dt, J=47.0, 16.0 Hz)

IR (KBr): 3334, 2988, 2946, 2919, 2848, 1495, 1450, 1324, 1135, 1079, 1017, 971, 885, 755, 695

MS (ESI, m/z)=167.0 (M+H$^-$)

Comparative Example 1

Using the same reaction apparatus as in Example 7, the same operations as in Example 1 were carried out, except that the 2-fluoro-1,3-benzodithiol 1,1,3,3-tetraoxide was changed to 1-fluorobis(phenylsulfonyl)methane. However, since the reaction did not proceed, the target 2-fluoro-2-(phenylhydroxymethyl)-1,3-benzodithiol 1,1,3,3-tetraoxide could not be obtained.

Example 10

Preparation of 2-fluoro-2-[(1S)-1-acetoxy-3-phenyl-2-butenyl]-1,3-benzodithiol 1,1,3,3-tetraoxide

[Formula 21]

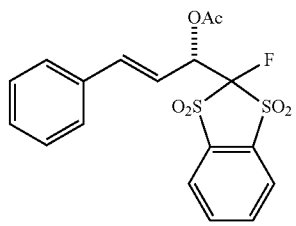

In a 10 ml flask provided with a stirrer, [Pd(C$_3$H$_5$)Cl]$_2$ (23.4 mg, 0.064 mmol), (R)-BINAP (79.8 mg, 0.13 mmol), and CH$_2$Cl$_2$ (0.85 ml) were added to 3,3-diacetyl-1-phenyl-1-propylene 2 (200 mg, 0.85 mmol), and the resultant mixture was stirred for 5 minutes at room temperature. Then 1b (222 mg, 0.94 mmol) and potassium carbonate (354 mg, 2.56 mmol) were added to the mixture, and the mixture was stirred for 20 hours. Then, a saturated ammonium chloride aqueous solution was added. The aqueous layer was extracted with dichloromethane. The organic layer was dried over anhydrous magnesium sulfate. The solvent was removed by distillation using an evaporator, and then the product was purified by silica gel column chromatography (hexane:ethyl acetate=7:3) to obtain 270 mg (77%, 91% ee) of the target 2-fluoro-2-[(1S)-1-acetoxy-3-phenyl-2-butenyl]-1,3-benzodithiol 1,1,3,3-tetraoxide.

Molecular weight: 410.44

R$_f$=0.18 (hexane:ethyl acetate=7:3)

$^1$H-NMR (CDCl$_3$, 200 MHz) δ: 2.22 (s, 3H), 6.24 (dd, J=15.8, 8.5 Hz, 1H), 6.69 (dd, 25, 8.5 Hz, 1H), 7.11 (dd, J=15.8 Hz, 1H), 7.31-7.50 (m, 5H), 7.93-8.08 (m, 4H)

$^{19}$F-NMR (CDCl$_3$, 188 MHz) δ: −160.35 (d, J=25.2 Hz, 1F)

HPLC AD-H column (n-hexane/1-PrOH=95/5, flow rate 2.0 ml/min, λ=254 nm, τ$_{min}$=31.7 min, τ$_{maj}$=34.8)

Example 11

Preparation of 2-fluoro-2-[(1S)-1-hydroxy-3-phenyl-2-butenyl]-1,3-benzodithiol 1,1,3,3-tetraoxide

[Formula 22]

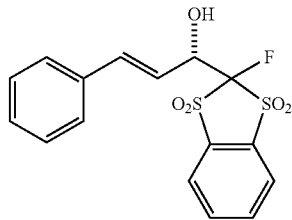

A 5 ml round-bottomed flask provided with a stirrer was charged with MeOH (5 ml) and the 2-fluoro-2-[(1S)-1-acetoxy-3-phenyl-2-butenyl]-1,3-benzodithiol 1,1,3,3-tetraoxide (265 mg, 0.64 mmol) obtained in Example 10 to form a suspension. Next, 3N hydrochloric acid (1.3 ml) was added to the suspension, and the resultant mixture was heated to reflux. After 24 hours, the solvent was removed by distillation. The aqueous layer was extracted with ethyl acetate. The organic layer was dried over anhydrous magnesium sulfate. The solvent was removed by distillation, and then the product was purified by silica gel column chromatography (hexane:ethyl acetate=7:3) to obtain 230.4 mg (98%, 91% ee) of the target 2-fluoro-2-[(1S)-1-hydroxy-3-phenyl-2-butenyl]-1,3-benzodithiol 1,1,3,3-tetraoxide.

Molecular weight: 368.40

R$_f$=0.13 (hexane:ethyl acetate=7:3)

$^1$H-NMR (CDCl$_3$, 200 MHz) δ: 2.78 (br., 1H), 5.71 (dd, J=23.9, 7.9 Hz, 1H), 6.37 (dd, 15.7, 7.5 Hz, 1H), 7.03 (d, J=16.0, 6.0 Hz, 1H), 7.30-7.50 (m, 5H), 7.91-8.10 (m, 4H)

$^{19}$F-NMR (CDCl$_3$, 188 MHz) δ: −164.7 (d, 23.3 Hz)

HPLC AD-H column (n-hexane/1-PrOH=70/30, flow rate 1.0 ml/min, λ=254 nm, τ$_{min}$=23.1 min, τ$_{maj}$=19.7)

Example 12

Preparation of (3S)-(E)-4-fluoro-3-hydroxy-1-phenyl-1-butene

[Formula 23]

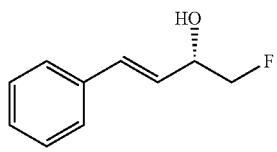

A 5 ml round-bottomed flask provided with a stirrer was charged with the 2-fluoro-2-[(1S)-1-hydroxy-3-phenyl-2-butenyl]-1,3-benzodithiol 1,1,3,3-tetraoxide (41.2 mg, 0.11 mmol, 91% ee) prepared in Example 11 and MeOH (2.0 ml). The resultant mixture was cooled to 40° C. Samarium(II) iodide/tetrahydrofuran (0.1 M, 6.7 ml) was slowly added dropwise, and the mixture was stirred for 1 hour. Then, a saturated ammonium chloride aqueous solution was added. The aqueous layer was extracted with dichloromethane. A sodium thiosulfate aqueous solution was added to the organic layer, and the organic layer was extracted. Then, the organic layer was dried over anhydrous magnesium sulfate. The solvent was removed by distillation using an evaporator, and then the product was purified by silica gel column chromatography (dichloromethane:methanol=95:5) to obtain 15.0 mg (81%, 90% ee) of the target (3S)-(E)-4-fluoro-3-hydroxy-1-phenyl-1-butene.

Molecular weight: 166.19

R$_f$=0.50 (dichloroethane:methanol=95:5)

$^1$H-NMR (CDCl$_3$, 200 MHz) δ: 2.21 (brd., 1H), 4.21-4.64 (ddd, J=47.8, 9.6, 7.5 Hz, 2H), 4.59 (brm., 1H), 6.15 (dd, J=16.0, 6.0 Hz, 1H), 6.74 (16.2 Hz)

$^{19}$F-NMR (CDCl$_3$, 188 MHz) δ: −224.6 (dt, 47.3, 16.0 Hz)

MS (ESI, m/z)=166 (M−H)

HPLC OJ-H column (n-hexane/1-PrOH=85/15, flow rate 0.5 ml/min, λ=254 nm, τ$_{min}$=16.5 min, τ$_{maj}$=18.2)

Reference Example 4

Preparation of (3S)-3-acetoxy-4-fluoro-1-phenyl-4,4-bis(phenylsulfonyl)-1-butene

[Formula 24]

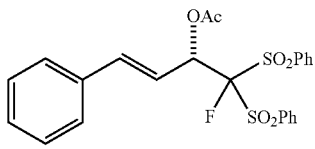

A 10 ml flask provided with a stirrer was charged with 3,3-diacetyl-1-phenyl-1-propylene (23.4 mg, 0.1 mmol), allylpalladium(II) chloride ([Pd(C$_3$H$_5$)Cl]$_2$, 1.1 mg, 0.003 mmol), and (R)-(+)-2,2'-dimethoxy-6,6'-bis(diphenylphosphino)-1,1'-biphenyl (hereinafter, abbreviated to MeO-BIPHEP, 5.8 mg, 0.01 mmol), and dimethoxyethane (0.1 ml), and the resultant mixture was stirred for 5 minutes at room temperature. Then, 1-fluorobis(phenylsulfonyl)methane (1), (37.7 mg, 0.12 mmol) and cesium carbonate (58.6 mg, 0.18 mmol) were added to the mixture, and the mixture was allowed to react under stirring for 6 hours at the same temperature. After the reaction was finished, a saturated ammonium chloride aqueous solution was added. The aqueous layer was extracted with dichloromethane. The organic layers were combined and dried over anhydrous magnesium sulfate, filtered, concentrated, and then purified by silica gel column chromatography (hexane:acetone=9:1) to obtain 45.3 mg (93%, 94% ee) of the target (3S)-3-acetoxy-4-fluoro-1-phenyl-4,4-bis(phenylsulfonyl)-1-butene.
Molecular weight: 488.55
R$_f$=0.35 (hexane:acetone=7:3)
$^1$H-NMR (CDCl$_3$, 200 MHz) δ: 1.87 (s, 3H), 6.31 (m, 3H), 7.27-7.75 (m, 11H), 7.98 (dd, J=20.8, 8.0 Hz, 4H)
$^{13}$C-NMR (CDCl$_3$, 50.3 MHz) δ: 21.1, 72.6 (d, J=23.1 Hz), 112.3 (d, J=268.2 Hz), 119.1, 127.4, 128.8, 128.9, 129.0, 129.2, 131.5 (dd, J=20.0, 1.2 Hz), 135.5, 136.2, 136.4, 138.6, 168.6
$^{19}$F-NMR (CDCl$_3$, 188 MHz) δ: −137.3 (d, 5.3 Hz, 1F)
IR (KBr) 3071, 2929, 1741, 1583, 1449, 1352, 1222, 1153, 1098, 978, 757, 680, 590, 537 cm$^{-1}$
MS (ESI, m/z)=527.0 (M+K$^+$), 511.0 (M+Na$^+$)
HPLC AD-H column (n-hexane/1-PrOH=80/20, flow rate 0.3 ml/min, λ=254 nm, τ$_{min}$=75.3 min, τ$_{maj}$=45.9)

Comparative Example 2

[Formula 25]

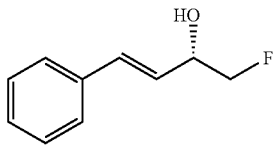

In a 5 ml round-bottomed flask provided with a stirrer, MeOH (10 ml) was added to the (3S)-3-acetoxy-4-fluoro-1-phenyl-4,4-bis(phenylsulfonyl)-1-butene (200 mg, 0.41 mmol, 94% ee) prepared in Reference Example 4, and the resultant mixture was cooled to −40° C. Then, samarium(II) iodide/tetrahydrofuran (0.1 M, 41 ml) was slowly added dropwise, and the mixture was stirred for 6 hours. Then, a saturated ammonium chloride aqueous solution was added. The aqueous layer was extracted with dichloromethane. A sodium thiosulfate aqueous solution was added to the organic layer, and the mixture was extracted. Then, the organic layer was dried over anhydrous magnesium sulfate. The solvent was removed by distillation using an evaporator, and then complete removal of the salt was carried out by silica gel column chromatography (ethyl acetate). Next, a magnesium ribbon (164 mg, 6.73 mmol) was activated by a heat gun in a nitrogen atmosphere, then left to cool at room temperature. Then, the magnesium ribbon was cooled to 0° C., and MeOH (0.5 ml) was added. Then, a solution of the crude product, which had been dried, in MeOH (2.0 ml) was added to the mixture, and then the mixture was stirred. After 1 hour, a saturated ammonium chloride aqueous solution was added. The aqueous layer was extracted with dichloromethane. The organic layer was dried over anhydrous magnesium sulfate. The solvent was removed by distillation using an evaporator, and then the product was purified by preparative thin-layer chromatography (dichloromethane:methanol=95:5) to obtain the target (3S)-(E)-4-fluoro-3-hydroxy-1-phenyl-1-butene. However, the isolated yield was low, at 30% (20.4 mg, 93% ee).

Comparative Example 3

The (3S)-3-acetoxy-4-fluoro-1-phenyl-4,4-bis(phenylsulfonyl)-1-butene prepared in Reference Example 4 was subjected to a deacetylation reaction based on the same operations as in Example 11. However, side reactions were prevalent, so that the target (3S)-3-hydroxy-4-fluoro-1-phenyl-4,4-bis(phenylsulfonyl)-1-butene was not obtained at all.

Industrial Applicability

The 2-fluoro-1,3-benzodithiol 1,1,3,3-tetraoxide derivative represented by the general formula (1) according to the present invention is an excellent monofluoromethyl group introduction agent. The monofluoromethyl group-containing compound derived using this compound can be effectively used as an intermediate in pharmaceutical and agrochemical synthesis.

The invention claimed is:
1. A 2-fluoro-1,3-benzodithiol 1,1,3,3-tetraoxide compound represented by the following formula (1),

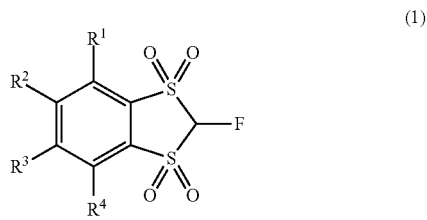

(1)

wherein:
R$^1$, R$^2$, R$^3$, and R$^4$ each independently represent a hydrogen atom, a straight-chain or branched alkyl group having 1 to 4 carbon atoms, a straight-chain or branched alkyloxy group having 1 to 4 carbon atoms, a halogen atom, a nitro group, or a cyano group.

2. The 2-fluoro-1,3-benzodithiol 1,1,3,3-tetraoxide according to claim 1, wherein $R^1$, $R^2$, $R^3$, and $R^4$ are all a hydrogen atom.

3. A method for producing the 2-fluoro-1,3-benzodithiol 1,1,3,3-tetraoxide compound according to claim 1,
comprising reacting a 1,3-benzodithiol 1,1,3,3-tetraoxide compound represented by the following formula (2),

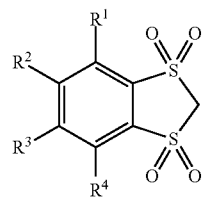

wherein $R^1$, $R^2$, $R^3$, and $R^4$ are as defined in claim 1, with an electrophilic fluorinating agent selected from the group consisting of:
1-chloromethyl-4-fluoro-1,4-diazabicyclo[2.2.2]octane bis(tetrafluoroborate),
N-fluoro-2,4,6-trimethylpyridinium tetrafluoroborate,
N-fluoropyridinium tetrafluoroborate,
N-fluoro-2,6-dichloropyridinium tetrafluoroborate,
N-fluoro-2,4,6-trimethylpyridinium trifluoromethanesulfonate,
N-fluoropyridinium trifluoromethanesulfonate,
N-fluoro-2,6-dichloropyridinium trifluoromethanesulfonate,
1,1'-difluoro-2,2'-bipyridinium bis(tetrafluoroborate),
N-fluoro-4,6-dimethylpyridinium-2-sulfonate,
N-fluoro-4-methylpyridinium-2-sulfonate,
N-fluoro-5-(trifluoromethyl)pyridinium-2-sulfonate,
N-fluoro-3-chloro-5-(trifluoromethyl)pyridinium-2-sulfonate, and
N-fluoro-4,6-bis(trifluoromethyl)pyridinium-2-sulfonate.

4. A method for producing a 2-substituted-2-fluoro-1,3-benzodithiol 1,1,3,3-tetraoxide compound represented by the following formula (4),

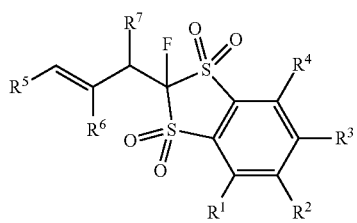

wherein:
$R^1$, $R^2$, $R^3$, and $R^4$ each independently represent a hydrogen atom, a straight-chain or branched alkyl group having 1 to 4 carbon atoms, a straight-chain or branched alkyloxy group having 1 to 4 carbon atoms, a halogen atom, a nitro group, or a cyano group;
$R^5$ represents a hydrogen atom, a methyl group, an ethyl group, a straight-chain, branched, or cyclic alkyl group having 3 to 10 carbon atoms, an optionally-substituted phenyl group, a 1-naphthyl group, or a 2-naphthyl group;
$R^6$ represents a hydrogen atom, a methyl group, an ethyl group, an n-propyl group, an isopropyl group, or a benzyl group; and
$R^7$ represents a hydrogen atom, a methyl group, an ethyl group, a straight-chain, branched, or cyclic alkyl group having 3 to 10 carbon atoms, a phenyl group, an acetoxy group, a methoxy group, an ethoxy group, or a straight-chain, branched, or cyclic alkyloxy group having 3 to 10 carbon atoms, the method comprising:
reacting, in the presence of a metal catalyst, an acetate represented by the following formula (3),

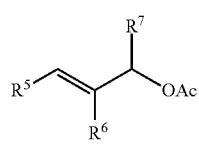

wherein $R^5$, $R^6$, and $R^7$ are as defined above,
with the 2-fluoro-1,3-benzodithiol 1,1,3,3-tetraoxide compound represented by the formula (1) according to claim 1,
to obtain the 2-substituted-2-fluoro-1,3-benzodithiol 1,1,3,3-tetraoxide compound represented by the formula (4).

5. The method for producing the 2-substituted-2-fluoro-1,3-benzodithiol 1,1,3,3-tetraoxide compound according to claim 4, wherein $R^1$, $R^2$, $R^3$, and $R^4$ are a hydrogen atom and $R^7$ is an acetoxy group.

6. A method for producing a monofluoromethyl group-containing compound represented by the following formula (5),

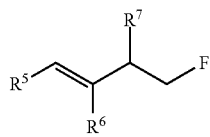

wherein:

$R^5$ represents a hydrogen atom, a methyl group, an ethyl group, a straight-chain, branched, or cyclic alkyl group having 3 to 10 carbon atoms, an optionally-substituted phenyl group, a 1-naphthyl group, or a 2-naphthyl group;

$R^6$ represents a hydrogen atom, a methyl group, an ethyl group, an n-propyl group, an isopropyl group, or a benzyl group; and $R^7$ represents a hydrogen atom, a methyl group, an ethyl group, a straight-chain, branched, or cyclic alkyl group having 3 to 10 carbon atoms, a phenyl group, an acetoxy group, a methoxy group, an ethoxy group, or a straight-chain, branched, or cyclic alkyloxy group having 3 to 10 carbon atoms, the method comprising:

reacting, in the presence of a metal catalyst, an acetate represented by the following formula (3),

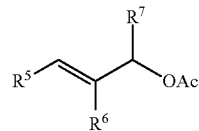

(3)

wherein $R^5$, $R^6$ and $R^7$ are as defined above, with the 2-fluoro-1,3-benzodithiol 1,1,3,3-tetraoxide compound represented by the formula (1) according to claim 1, to obtain a 2-substituted-2-fluoro-1,3-benzodithiol 1,1,3,3-tetraoxide compound represented by the following formula (4),

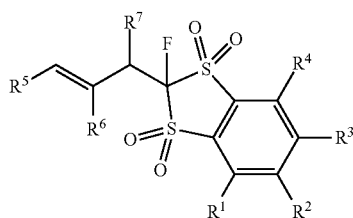

(4)

wherein:

$R^1$, $R^2$, $R^3$, and $R^4$ each independently represent a hydrogen atom, a straight-chain or branched alkyl group having 1 to 4 carbon atoms, a straight-chain or branched alkyloxy group having 1 to 4 carbon atoms, a halogen atom, a nitro group, or a cyano group; and $R^5$, $R^6$ and $R^7$ are as defined above, and then reducing the compound represented by the formula (4) to obtain the monofluoromethyl group-containing compound represented by the formula (5).

7. A method for producing a monofluoromethyl group-containing compound represented by the following formula (6),

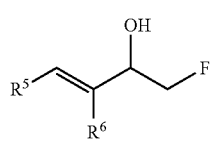

(6)

wherein:

$R^5$ represents a hydrogen atom, a methyl group, an ethyl group, a straight-chain, branched, or cyclic alkyl group having 3 to 10 carbon atoms, an optionally-substituted phenyl group, a 1-naphthyl group, or a 2-naphthyl group; and $R^6$ represents a hydrogen atom, a methyl group, an ethyl group, an n-propyl group, an isopropyl group, or a benzyl group;

the method comprising:

(1) first producing a 2-substituted-2-fluoro-1,3-benzodithiol 1,1,3,3-tetraoxide compound represented by the following formula (4),

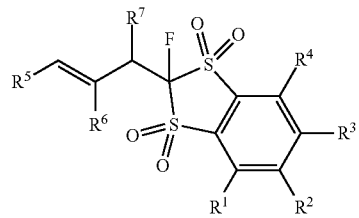

(4)

wherein:

$R^1$, $R^2$, $R^3$, and $R^4$ are each a hydrogen atom;

$R^5$ and $R^6$ are as defined above; and $R^7$ is an acetoxy group, by reacting, in the presence of a metal catalyst, an acetate represented by the following formula (3),

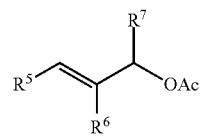

(3)

wherein $R^5$, $R^6$, and $R^7$ are as defined above, with a 2-fluoro-1,3-benzodithiol 1,1,3,3-tetraoxide compound represented by the following formula (1),

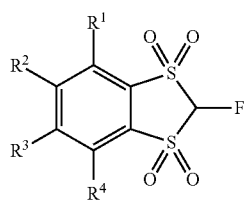

(1)

wherein $R^1$, $R^2$, $R^3$, and $R^4$ are as defined above, to obtain the 2-substituted-2-fluoro-1,3-benzodithiol 1,1,3,3-tetraoxide compound represented by the formula (4), and (2) then hydrolyzing the compound represented by the formula (4) to obtain the monofluoromethyl group-containing compound represented by the formula (6).

8. A method for producing an optically-active 2-substituted-2-fluoro-1,3-benzodithiol 1,1,3,3-tetraoxide compound represented by the following formula (7),

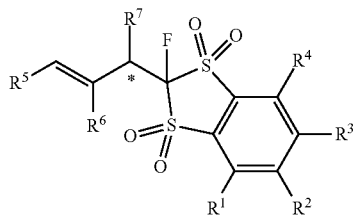

(7)

wherein:

* represents an asymmetric carbon;

$R^1$, $R^2$, $R^3$, and $R^4$ each independently represent a hydrogen atom, a straight-chain or branched alkyl group having 1 to 4 carbon atoms, a straight-chain or branched alkyloxy group having 1 to 4 carbon atoms, a halogen atom, a nitro group, or a cyano group;

$R^5$ represents a hydrogen atom, a methyl group, an ethyl group, a straight-chain, branched, or cyclic alkyl group having 3 to 10 carbon atoms, an optionally-substituted phenyl group, a 1-naphthyl group, or a 2-naphthyl group;

$R^6$ represents a hydrogen atom, a methyl group, an ethyl group, an n-propyl group, an isopropyl group, or a benzyl group; and $R^7$ represents a hydrogen atom, a methyl group, an ethyl group, a straight-chain, branched, or cyclic alkyl group having 3 to 10 carbon atoms, a phenyl group, an acetoxy group, a methoxy group, an ethoxy group, or a straight-chain, branched, or cyclic alkyloxy group having 3 to 10 carbon atoms, the method comprising:

reacting, in the presence of an optically active ligand and a metal catalyst, an acetate represented by the following formula (3),

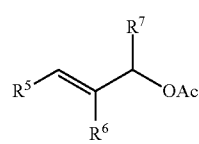

(3)

wherein $R^5$, $R^6$, and $R^7$ are as defined above, with the 2-fluoro-1,3-benzodithiol 1,1,3,3-tetraoxide compound represented by the formula (1) according to claim 1, to obtain the optically-active 2-substituted-2-fluoro-1,3-benzodithiol 1,1,3,3-tetraoxide compound represented by the formula (7).

9. The method for producing the optically-active 2-substituted-2-fluoro-1,3-benzodithiol 1,1,3,3-tetraoxide compound represented by the formula (7) according to claim 8, wherein $R^1$, $R^2$, $R^3$, and $R^4$ are a hydrogen atom and $R^7$ is an acetoxy group.

10. A method for producing an optically-active monofluoromethyl group-containing compound represented by the following formula (8),

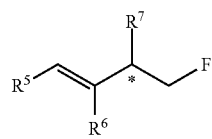

(8)

wherein:

* represents an asymmetric carbon;

$R^5$ represents a hydrogen atom, a methyl group, an ethyl group, a straight-chain, branched, or cyclic alkyl group having 3 to 10 carbon atoms, an optionally-substituted phenyl group, a 1-naphthyl group, or a 2-naphthyl group;

$R^6$ represents a hydrogen atom, a methyl group, an ethyl group, an n-propyl group, an isopropyl group, or a benzyl group; and $R^7$ represents a hydrogen atom, a methyl group, an ethyl group, a straight-chain, branched, or cyclic alkyl group having 3 to 10 carbon atoms, a phenyl group, an acetoxy group, a methoxy group, an ethoxy group, or a straight-chain, branched, or cyclic alkyloxy group having 3 to 10 carbon atoms, the method comprising:

(1) first producing an optically-active 2-substituted-2-fluoro-1,3-benzodithiol 1,1,3,3-tetraoxide compound represented by the following formula (7),

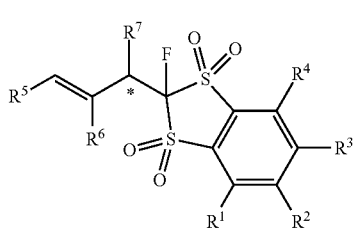

(7)

wherein:

$R^1$, $R^2$, $R^3$, and $R^4$ each independently represent a hydrogen atom, a straight-chain or branched alkyl group having 1 to 4 carbon atoms, a straight-chain or branched alkyloxy group having 1 to 4 carbon atoms, a halogen atom, a nitro group, or a cyano group; and

*, $R^5$, $R^6$, and $R^7$ are as defined above, by reacting, in the presence of an optically active ligand and a metal catalyst, an acetate represented by the following formula (3),

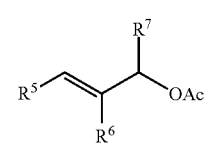

(3)

wherein $R^5$, $R^6$, and $R^7$ are as defined above,
with the 2-fluoro-1,3-benzodithiol 1,1,3,3-tetraoxide compound represented by the formula (1) according to claim 1,
to obtain the optically-active 2-substituted-2-fluoro-1,3-benzodithiol 1,1,3,3-tetraoxide compound represented by the formula (7), and (2) then hydrolyzing the compound represented by the formula (7) to obtain a hydrolyzed product, and (3) then reducing the hydrolyzed product to obtain the optically-active monofluoromethyl group-containing compound represented by the formula (8).

11. A method for producing an optically-active monofluoromethyl group-containing compound represented by the following formula (9),

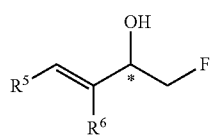

(9)

wherein:
* represents an asymmetric carbon;
$R^5$ represents a hydrogen atom, a methyl group, an ethyl group, a straight-chain, branched, or cyclic alkyl group having 3 to 10 carbon atoms, an optionally -substituted phenyl group, a 1-naphthyl group, or a 2-naphthyl group; and
$R^6$ represents a hydrogen atom, a methyl group, an ethyl group, an n-propyl group, an isopropyl group, or a benzyl group,
the method comprising:

(1) first producing an optically-active 2-substituted-2-fluoro-1,3-benzodithiol 1,1,3,3-tetraoxide compound represented by the following formula (7),

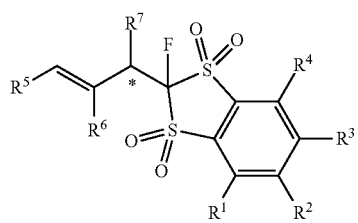

(7)

wherein:
*, $R^5$ and $R^6$ are as defined above;
$R^1$, $R^2$, $R^3$, and $R^4$ are each a hydrogen atom; and
$R^7$ represents an acetoxy group,
by reacting, in the presence of an optically active ligand and a metal catalyst, an acetate represented by the following formula (3),

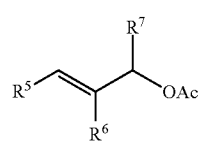

(3)

wherein $R^5$, $R^6$, and $R^7$ are as defined above,
with the 2-fluoro-1,3-benzodithiol 1,1,3,3-tetraoxide compound represented by the formula (1) according to claim 1,
to obtain the optically-active 2-substituted-2-fluoro-1,3-benzodithiol 1,1,3,3-tetraoxide compound represented by the formula (7), and (2) then hydrolyzing the compound represented by the formula (7) to obtain a hydrolyzed product, and (3) then reducing the hydrolyzed product to obtain the optically-active monofluoromethyl group-containing compound represented by the formula (9).

12. A method for producing a 2-substituted-2-fluoro-1,3-benzodithiol 1,1,3,3-tetraoxide compound represented by the following formula (11),

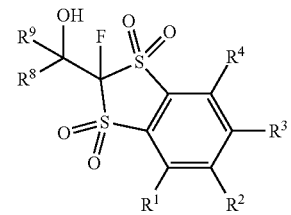

(11)

wherein:
$R^1$, $R^2$, $R^3$, and $R^4$ each independently represent a hydrogen atom, a straight-chain or branched alkyl group having 1 to 4 carbon atoms, a straight-chain or branched alkyloxy group having 1 to 4 carbon atoms, a halogen atom, a nitro group, or a cyano group;
$R^8$ and $R^9$ each independently represents a hydrogen atom, a methyl group, an ethyl group, a straight-chain, branched, or cyclic alkyl group having 3 to 10 carbon atoms, an optionally-substituted phenyl group, a 1-naphthyl group, a 2-naphthyl group, or a phenylethylene group; and $R^8$ and $R^9$ are not simultaneously a hydrogen atom, the method comprising:

reacting, in the presence of a base, a carbonyl-containing compound represented by the following formula (10),

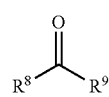

(10)

wherein $R^8$ and $R^9$ are as described above, with the 2-fluoro-1,3-benzodithiol 1,1,3,3-tetraoxide compound represented by the formula (1) according to claim 1,
to obtain the 2-substituted-2-fluoro-1,3-benzodithiol 1,1,3,3-tetraoxide compound represented by the formula (11).

13. The method for producing the 2-substituted-2-fluoro-1,3-benzodithiol 1,1,3,3-tetraoxide derivative according to claim 12, wherein $R^1$, $R^2$, $R^3$, $R^4$, and $R^9$ are a hydrogen atom.

14. A method for producing a monofluoromethyl group-containing compound represented by the following formula (12),

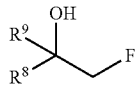
(12)

wherein:
R⁸ and R⁹ each independently represents a hydrogen atom, a methyl group, an ethyl group, a straight-chain, branched, or cyclic alkyl group having 3 to 10 carbon atoms, an optionally-substituted phenyl group, a 1-naphthyl group, a 2-naphthyl group, or a phenylethylene group; and R⁸ and R⁹ are not simultaneously a hydrogen atom,
the method comprising:
(1) first producing a 2-substituted-2-fluoro-1,3-benzodithiol 1,1,3,3-tetraoxide compound represented by the following formula (11),

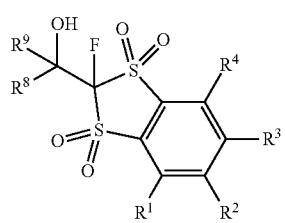
(11)

wherein:
R¹, R², R³, and R⁴ each independently represent a hydrogen atom, a straight-chain or branched alkyl group having 1 to 4 carbon atoms, a straight-chain or branched alkyloxy group having 1 to 4 carbon atoms, a halogen atom, a nitro group, or a cyano group;
R⁸ and R⁹ each independently represents a hydrogen atom, a methyl group, an ethyl group, a straight-chain, branched, or cyclic alkyl group having 3 to 10 carbon atoms, an optionally-substituted phenyl group, a 1-naphthyl group, a 2-naphthyl group, or a phenylethylene group; and R⁸ and R⁹ are not simultaneously a hydrogen atom,
by reacting, in the presence of a base, a carbonyl-containing compound represented by the following formula (10),

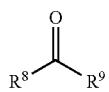
(10)

wherein R⁸ and R⁹ are as defined above,
with the 2-fluoro-1,3-benzodithiol 1,1,3,3-tetraoxide compound represented by the formula (1) according to claim 1,
to obtain the 2-substituted-2-fluoro-1,3-benzodithiol 1,1,3,3-tetraoxide compound represented by the formula (11), and (2) then reducing the compound of the formula (11) to obtain the monofluoromethyl group-containing compound represented by the formula (12).

15. A method for producing a monofluoromethyl group-containing compound represented by the following formula (13),

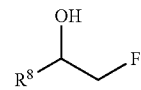
(13)

wherein R⁸ represents a hydrogen atom, a methyl group, an ethyl group, a straight-chain, branched, or cyclic alkyl group having 3 to 10 carbon atoms, an optionally-substituted phenyl group, a 1-naphthyl group, a 2-naphthyl group, or a phenylethylene group,
the method comprising:
(1) first producing a 2-substituted-2-fluoro-1,3-benzodithiol 1,1,3,3-tetraoxide compound represented by the following formula (11),

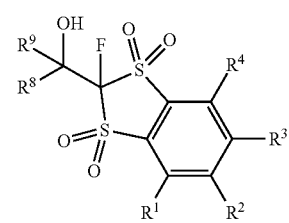
(11)

wherein:
R¹, R², R³, R⁴, and R⁹ each represent a hydrogen atom; and
R⁸ represents a methyl group, an ethyl group, a straight-chain, branched, or cyclic alkyl group having 3 to 10 carbon atoms, an optionally-substituted phenyl group, a 1-naphthyl group, a 2-naphthyl group, or a phenylethylene group,
by reacting, in the presence of a base, a carbonyl-containing compound represented by the following formula (10),

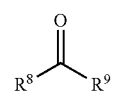
(10)

wherein R⁸ and R⁹ are as defined above,
with the 2-fluoro-1,3-benzodithiol 1,1,3,3-tetraoxide compound represented by the formula (1) according to claim 1,
to obtain the 2-substituted-2-fluoro-1,3-benzodithiol 1,1,3,3-tetraoxide compound represented by the formula (11), and
(2) then reducing the compound represented by the formula (11) to obtain the monofluoromethyl group-containing compound represented by the formula (13).

* * * * *